(12) United States Patent
Beers et al.

(10) Patent No.: US 7,999,809 B2
(45) Date of Patent: Aug. 16, 2011

(54) COMPUTER SYSTEMS AND METHODS FOR AUTOMATIC GENERATION OF MODELS FOR A DATASET

(75) Inventors: Andrew C. Beers, San Francisco, CA (US); Matthew W. Eldridge, Seattle, WA (US); Patrick M. Hanrahan, Portola Valley, CA (US); Jonathan E. Taylor, Stanford, CA (US)

(73) Assignee: Tableau Software, Inc., Seattle, WA (US)

( * ) Notice: Subject to any disclaimer, the term of this patent is extended or adjusted under 35 U.S.C. 154(b) by 0 days.

(21) Appl. No.: 11/787,761

(22) Filed: Apr. 17, 2007

(65) Prior Publication Data
US 2007/0250523 A1    Oct. 25, 2007

Related U.S. Application Data

(60) Provisional application No. 60/793,701, filed on Apr. 19, 2006.

(51) Int. Cl.
*G06T 11/20* (2006.01)
(52) U.S. Cl. .................................. 345/440; 707/899
(58) Field of Classification Search .................. 345/440; 707/100, 104.1, 102
See application file for complete search history.

(56) References Cited

U.S. PATENT DOCUMENTS

| | | | |
|---|---|---|---|
| 4,800,810 A | 1/1989 | Masumoto | 99/519 |
| 5,036,314 A | 7/1991 | Barillari et al. | 340/717 |
| 5,060,980 A | 10/1991 | Johnson et al. | 283/70 |
| 5,143,888 A * | 9/1992 | Olbrich | 502/329 |
| 5,144,452 A | 9/1992 | Abuyama | 358/296 |
| 5,169,713 A | 12/1992 | Kumurdjian | 428/323 |
| 5,265,244 A | 11/1993 | Ghosh et al. | 395/600 |
| 5,265,246 A | 11/1993 | Li et al. | 395/600 |
| 5,377,348 A | 12/1994 | Lau et al. | 395/600 |
| 5,383,029 A | 1/1995 | Kojima | 358/403 |
| 5,560,007 A | 9/1996 | Thai | 395/600 |
| 5,577,241 A | 11/1996 | Spencer | 395/605 |
| 5,581,677 A | 12/1996 | Myers et al. | 395/140 |
| 5,664,172 A | 9/1997 | Antoshenkov | 395/604 |
| 5,664,182 A | 9/1997 | Nierenberg et al. | 395/613 |
| 5,668,987 A | 9/1997 | Schneider | 395/603 |
| 5,794,246 A | 8/1998 | Sankaran et al. | 707/101 |
| 5,864,856 A | 1/1999 | Young | 707/100 |

(Continued)

FOREIGN PATENT DOCUMENTS

HU    215657 B    1/1994

(Continued)

OTHER PUBLICATIONS

Becker, "Visualizing Decision Table Classifiers", Proceedings IEEE Symposium on Information Visualization, pp. 102-105, 1998.

(Continued)

*Primary Examiner* — Hung T Vy
(74) *Attorney, Agent, or Firm* — Morgan, Lewis & Bockius LLP

(57) ABSTRACT

A method of automatically generating models from a dataset includes multiple steps. First, a description of a view of a dataset is provided. The description includes multiple fields associated with the dataset. Next, a set of properties is determined for each of the multiple fields. Finally, the description is automatically translated into one or more models based on the respective properties of the multiple fields and a set of predefined heuristics.

66 Claims, 17 Drawing Sheets

U.S. PATENT DOCUMENTS

| | | | |
|---|---|---|---|
| 5,893,088 A | 4/1999 | Hendricks et al. | 707/3 |
| 5,933,830 A | 8/1999 | Williams | 707/100 |
| 6,031,632 A | 2/2000 | Yoshihara et al. | 358/403 |
| 6,032,158 A | 2/2000 | Mukhopadhyay et al. | 707/201 |
| 6,044,374 A | 3/2000 | Nesamoney et al. | 707/10 |
| 6,100,901 A | 8/2000 | Mohda et al. | 345/440 |
| 6,115,744 A | 9/2000 | Robins et al. | 709/227 |
| 6,154,766 A | 11/2000 | Yost et al. | 709/201 |
| 6,173,310 B1 | 1/2001 | Yost et al. | 709/201 |
| 6,188,403 B1 | 2/2001 | Sacerdoti et al. | 345/339 |
| 6,208,990 B1 | 3/2001 | Suresh et al. | 707/6 |
| 6,222,540 B1 | 4/2001 | Sacerdoti | 345/339 |
| 6,247,008 B1 | 6/2001 | Cambot et al. | 707/3 |
| 6,253,257 B1 | 6/2001 | Dundon | 709/331 |
| 6,260,050 B1 | 7/2001 | Yost et al. | 707/501 |
| 6,269,393 B1 | 7/2001 | Yost et al. | 709/201 |
| 6,300,957 B1 | 10/2001 | Rao et al. | 345/441 |
| 6,301,579 B1 | 10/2001 | Becker | 707/102 |
| 6,317,750 B1 | 11/2001 | Tortolani et al. | 707/103 |
| 6,327,628 B1 | 12/2001 | Anuff et al. | 709/311 |
| 6,339,775 B1 | 1/2002 | Zamanian et al. | 707/101 |
| 6,377,259 B1 | 4/2002 | Tenev et al. | 345/440 |
| 6,397,195 B1 | 5/2002 | Pinard et al. | 705/30 |
| 6,400,366 B1 | 6/2002 | Davies et al. | 345/440 |
| 6,405,195 B1 | 6/2002 | Ahlberg | 707/4 |
| 6,405,208 B1 | 6/2002 | Raghavan et al. | 707/102 |
| 6,424,933 B1 | 7/2002 | Agrawala et al. | 703/2 |
| 6,490,593 B2 | 12/2002 | Proctor | 707/102 |
| 6,492,989 B1 | 12/2002 | Wilkinson | 345/440 |
| 6,522,342 B1 | 2/2003 | Gagnon et al. | 345/716 |
| 6,611,825 B1 | 8/2003 | Billheimer et al. | 706/45 |
| 6,643,646 B2 | 11/2003 | Su et al. | 707/6 |
| 6,707,454 B1 * | 3/2004 | Barg et al. | 345/440 |
| 6,714,897 B2 | 3/2004 | Whitney et al. | 702/189 |
| 6,725,230 B2 | 4/2004 | Ruth et al. | 707/102 |
| 6,750,864 B1 | 6/2004 | Anwar | 345/440 |
| 6,763,308 B2 * | 7/2004 | Chu et al. | 702/19 |
| 6,768,986 B2 | 7/2004 | Cras et al. | 707/2 |
| 6,906,717 B2 | 6/2005 | Couckuyt et al. | 345/440 |
| 7,009,609 B2 | 3/2006 | Miyadai | 345/440 |
| 7,089,266 B2 * | 8/2006 | Stolte et al. | 707/104.1 |
| 7,117,058 B2 | 10/2006 | Lin et al. | 700/108 |
| 7,315,305 B2 | 1/2008 | Crotty et al. | 345/440 |
| 7,379,601 B2 | 5/2008 | Yang et al. | 382/224 |
| 2002/0016699 A1* | 2/2002 | Hoggart et al. | 703/2 |
| 2002/0118192 A1 | 8/2002 | Couckuyt et al. | 345/440 |
| 2002/0123865 A1 | 9/2002 | Whitney et al. | 702/189 |
| 2002/0154118 A1 | 10/2002 | McCarthy et al. | 345/440 |
| 2003/0042928 A1* | 3/2003 | Tsai | 324/769 |
| 2003/0200034 A1 | 10/2003 | Fellenberg et al. | 702/20 |
| 2004/0183800 A1 | 9/2004 | Peterson | 345/440 |
| 2004/0224577 A1* | 11/2004 | Kaji | 440/1 |
| 2004/0227759 A1 | 11/2004 | McKnight et al. | 345/440 |
| 2004/0243593 A1* | 12/2004 | Stolte et al. | 707/100 |
| 2005/0035966 A1 | 2/2005 | Pasquarette et al. | 345/440 |
| 2005/0035967 A1 | 2/2005 | Joffrain et al. | 345/440 |
| 2005/0060300 A1* | 3/2005 | Stolte et al. | 707/3 |
| 2005/0099423 A1 | 5/2005 | Brauss | 345/440 |
| 2005/0234688 A1* | 10/2005 | Pinto et al. | 703/6 |
| 2005/0234920 A1* | 10/2005 | Rhodes | 707/10 |
| 2006/0053363 A1* | 3/2006 | Bargh et al. | 715/503 |
| 2006/0100873 A1* | 5/2006 | Bittner et al. | 704/256.2 |
| 2006/0129913 A1* | 6/2006 | Vigesaa et al. | 715/503 |
| 2006/0136825 A1 | 6/2006 | Cory et al. | 715/700 |
| 2006/0206512 A1* | 9/2006 | Hanrahan et al. | 707/102 |
| 2007/0055487 A1* | 3/2007 | Habitz et al. | 703/19 |
| 2007/0061344 A1* | 3/2007 | Dickerman et al. | 707/100 |
| 2008/0133573 A1* | 6/2008 | Haft et al. | 707/102 |

FOREIGN PATENT DOCUMENTS

| | | |
|---|---|---|
| WO | WO 2006/060773 A2 | 6/2006 |

OTHER PUBLICATIONS

Becker et al., "Trellis Graphics Displays: A Multi-Dimensional Data Visualization Tool for Data Mining," Third Annual Conference on Knowledge Discovery in Databases, Aug. 1997.

Bosch et al., "Performance Analysis and Visualization of Parallel Systems Using SimOS and Rivet: A Case Study," Proceedings of the Sixth IEEE International Symposium on High-Performance Computer Architecture, pp. 360-371, Jan. 2000.

Bosch et al., "Rivet: A Flexible Environment for Computer Systems Visualization," Computer Graphics 34, pp. 68-73, Feb. 2000.

Brunk et al., "MineSet: An Integrated System for Data Mining," Proceeding of the 3rd International Conference on Knowledge Discovery and Data Mining, pp. 135-138, AAAI Press, 1997.

Derthick et al., "An Interactive Visual Query Environment for Exploring Data," Proceedings of ACM SIGGRAPH Symposium on User Interface Software & Technology, pp. 189-198, 1997.

Freeze, Unlocking OLAP with Microsoft SQL Server and Excel 2000, IDG Books Worldwide, Foster City, CA, pp. 155-332 and 379-422.

Fua et al., "Navigating Hierarchies with Structure-Based Brushes," Proc. of Infois '99 (San Francisco, CA, USA, 1999), IEEE Computer Soc. Press.

Goldstein et al., "A Framework for Knowledge-Based Interactive Data Exploration," Journal of Visual Languages and Computing 5, pp. 339-363, Dec. 1994.

Gray et al., "Data Cube: A Relational Aggregation Operator Generalizing Group-By, Cross-Tab, and Sub-Total," Data Mining and Knowledge Discovery 1, pp. 29-53, 1997.

Healey, "On the Use of Perceptual Cues and Data Mining for Effective Visualization of Scientific Datasets," Proceedings Graphics Interface '98, pp. 177-187.

Kohavi, "Data Mining and Visualization, " Frontiers of Engineering: Reports of leading-Edge Engineering from the 200 NAE Sym.

Livny et al., "DEVise: Integrated Querying and Visual Exploration of Large Datasets," Proceedings of ACM SIGMOD, pp. 301-312, May 1997.

MacDonald, "Creating Basic Charts," Excel 2003, Chapter 9, pp. 298-342, 2006.

MacKinlay, J., "Automating the Design of Graphical Presentations of Relational Informational," ACM Transactionss on Graphics 5(2), pp. 110-141, 1986.

Perlin et al., "An Alternative Approach to the Computer Interface," Proc. of the 20th International Conference on Computer Graphics and Interactive Techniques, pp. 57-64, 1993.

Rao et al., "The Table Lens: Merging Graphical and Symbolic Representations in an Interactive Focus+Context Visualization for Tabular Information," Proc. of ACM SIGCHI, Apr. 1994, pp. 318-322.

Roth et al., "Interactive Graphics Design Using Automatic Presentation Knowledge," Proceedings of the Conference on Human Factors in Computer Systems, Proc. SIGCHI '94, pp. 112-117, 1994.

Roth et al., "Visage: A User Interface Environment for Exploring Information" Proceedings of the International Visualization Symposium 1996, pp. 3-12, Mar. 12, 1999.

Screen Dumps for Microsoft Office Excel 2003 SP2, figures 1-24, 10 pp. 1-19.

Spenke et al., Focus: The Interactive Table for Product Comparison and Selection, Proc. of ACM Symposium on User Interface Software and Technology, Nov. 1996.

Stevens, "On the Theory of Scales of Measurement," Science vol. 103, No. 2684 pp. 677-680, Jun. 7, 1946.

Stolte et al., "Multiscale Visualization Using Data Cubes," Proceedings of the Eighth IEEE Symposium on Information Visualization, 2002.

Stolte et al., "Polaris: A System for Query, Analysis, and Visualization of Multidimensional Relational Databases," IEEE Transactions on Visualization and Computer Graphics 8(1), pp. 52-65, Jan. 2002.

Stolte et al, "Query, Analysis, and Visualization of Hierarchically Structured Data Using Polaris," Proceedings of the Eight ACM SIGKDD '02, International Conference on Knowledge Discovery and Data Mining, Jul. 2002.

Stolte et al., "Visualizing Application Behavior on Superscalar Processors," Proceedings of the IEEE Symposium on Information Visualization, pp. 10-17, 1999.

Thearling et al., "Visualizing Data Mining Models," Pub. in Information Visualization in Data Mining and Knowledge Discovery, Fayyad, Grinstein and Wierse, eds., Morgan Kaufman, 2001.

Welling et al., "Visualization of Large Multi-Dimensional Datasets," arXiv: astro-ph/0008186, Aug. 11, 2000.

Wilkinson, "Statistics and Computing-The Grammar of Graphics," Springer-Verlag, Inc., New York, 1999.

Wilkinson et al., "nViZn: An Algebra-Based Visualization System," Smart Graphics Symposium UK, Mar. 21-23, 2001, Hawthorne, NY USA.

Notice of Allowance for U.S. Appl. No. 10/453,834 dated Mar. 27, 2006.

Office Action for U.S. Appl. No. 10/667,194 dated Jun. 26, 2006.
Office Action for U.S. Appl. No. 10/667,194 dated Jan. 18, 2007.
Office Action for U.S. Appl. No. 10/667,194 dated Aug. 14, 2007.
Office Action for U.S. Appl. No. 10/667,194 dated Jan. 7, 2008.
Office Action for U.S. Appl. No. 10/667,194 dated Aug. 14, 2008.
Office Action for U.S. Appl. No. 10/667,194 dated Feb. 9, 2009.
Office Action for U.S. Appl. No. 11/005,652 dated Dec. 27, 2007.
Office Action for U.S. Appl. No. 11/005,652 dated Jul. 24, 2008.
Office Action for U.S. Appl. No. 11/005,652 dated Feb. 20, 2009.
Office Action for U.S. Appl. No. 11/223,658 dated May 21, 2008.
Office Action for U.S. Appl. No. 11/223,658 dated Feb. 23, 2009.
Office Action for U.S. Appl. No. 11/488,407 dated Apr. 3, 2009.
International Search Report and Written Opinion for PCT/US2004/30396 dated Aug. 24, 2006.
International Preliminary Report on Patentability for PCT/US2004/30396 dated Apr. 19, 2007.
International Search Report and Written Opinion for PCT/US2005/043937 dated Apr. 18, 2007.
International Preliminary Report on Patentability for PCT/US2005/043937 dated Jun. 14, 2007.
International Search Report and Written Opinion for PCT/US2007/009810 dated Jul. 7, 2008.
International Preliminary Report on Patentability for PCT/US2007/009810 dated Oct. 30, 2008.
International Search Report and Written Opinion for PCT/US2006/35300 dated Jul. 7, 2008.
International Search Report and Written Opinion for PCT/US04/18217 dated Feb. 7, 2006.
International Preliminary Report on Patentability for PCT/US04/18217 dated Oct. 19, 2006.
Hungarian Search Report for HU P0700460 dated Oct. 9, 2007.
Supplementary European Search Report for EP 04754739.3 dated Dec. 17, 2007.
Specification for U.S. Appl. No. 10/453,834, filed Jun. 2, 2003.
Specification for U.S. Appl. No. 11/005,652, filed Dec. 2, 2004.
Specification for U.S. Appl. No. 11/223,658, filed Sep. 5, 2005.

* cited by examiner

COMPUTER SYSTEMS AND METHODS FOR AUTOMATIC GENERATION OF MODELS FOR A DATASET

RELATED APPLICATIONS

This application claims priority to U.S. provisional Patent Application 60/793,701, "Computer Systems and Methods for Automatic Generation of Linear Models," filed on Apr. 19, 2006, which is hereby incorporated by reference in its entirety.

FIELD OF THE INVENTION

This invention relates generally to computer systems and methods for data visualization. The invention relates specifically to computer systems and methods for automatically generating and displaying data models derived from a multi-dimensional dataset.

BACKGROUND OF THE INVENTION

Multi-dimensional, large-scale datasets are found in diverse subjects, including gene expression data for uncovering the link between the human genome and the various proteins for which it codes; demographic and consumer profiling data for capturing underlying sociological and economic trends; sales and marketing data for huge numbers of products in vast and ever-changing marketplaces; and environmental data for understanding phenomena such as pollution, meteorological changes and resource impact issues.

One challenge for many users dealing with these datasets is how to extract the meaning from the data they contain: to discover structure, find patterns, and derive causal relationships. Very often, the sheer size and complexity of these datasets make it impossible for an analyst to directly glean any meaning from the data without employing some additional operations, such as regression, clustering, summarization, dependency modeling, and classification.

FIG. 1 is a prior art screenshot displaying a portion of a commercial dataset related to the sales and marketing activities of a soft drink company using Microsoft Excel. This dataset has dozens of data fields with different data types. For example, the data type of the "Date" field is time; the data type of the data fields like "Market", "State", and "Market Size" is text; and the data type of the data fields like "Sales", "Profit", and "Margin" is numeric value. There are many important information items embedded in the raw data; e.g., the most popular product in a state within a specific time period or the least profitable product from the marketing's perspective. But it is quite difficult to access any of them directly from the raw data.

In this regard, data visualization and statistical modeling are powerful tools for helping analysts to explore large datasets. Data visualization can represent a dataset or a portion of the dataset to meet an analyst's interest. For example, the analyst can gain insight into the company's marketing effort from a curve representing the relationship between the "Sales" and the "Marketing" data fields. In many instances, the mere visualization of raw data is not enough. Statistical modeling is often invoked to generate an analytical or numerical model from raw data. Statistical models can be used to predict values, e.g., through interpolation or extrapolation. Statistical models can also be used to test between alternative hypotheses. Hypothesis tests are widely used to confirm findings. In particular, the analyst can easily discover the trends of the market from visualizing the model. From analyzing the visualized model, the analyst can make informed business decisions.

A widely used type of statistical model is a linear model. Linear models relate a response variable to various quantitative and categorical factors using linear coefficients. A specific example of a linear model is linear regression where a y value is predicted from an x value. A special case of linear models is analysis of variance (ANOVA). In analysis of variance, mean values are predicted using factors. For example, the mean response to a drug may depend on the sex and age of the patient.

The conventional manner of generating and visualizing models from multi-dimensional datasets often requires a significant human-computer interaction. To do so, a user must be familiar with the characteristics of the dataset and must also provide detailed computer instructions to generate the models and visualizations. In many situations, a user may have to repeat the process several times to arrive at a satisfactory model. This is extremely inconvenient when a user deals with a large dataset having tens or even hundreds of data fields. The user may have to waste hours of time in order to uncover any significant trends embedded in the dataset.

Consequently, there is a strong need for improved methods and graphical user interfaces for generating and visualizing models.

SUMMARY OF THE INVENTION

The present invention provides improved methods for generating and visualizing models from a multi-dimensional dataset.

A first aspect of the invention provides a computer implemented method of automatically generating models from a dataset, comprising: providing a description of a view of a dataset that includes multiple fields associated with the dataset; determining a set of properties for each of the multiple fields; and automatically translating the description into one or more models based on the respective properties of the multiple fields and a set of predefined heuristics.

A second aspect of the invention provides a computer implemented method of automatically generating models from a dataset, comprising: allowing a user to provide a description that includes at least two sets of fields associated with a dataset; determining a set of properties for each of the two sets of fields; and automatically generating zero or more models based on the properties of the two sets of fields and a set of predefined heuristics.

A third aspect of the invention provides a computer system, comprising: a main memory; a processor; and at least one program stored in the main memory and executed by the processor, the at least one program further including: instructions for providing a description of a view of a dataset that includes multiple fields associated with the dataset; instructions for determining a set of properties for each of the multiple fields; and instructions for automatically translating the description into one or more models based on the respective properties of the multiple fields and a set of predefined heuristics.

A fourth aspect of the invention provides a computer program product for use in conjunction with a computer system, comprising: a computer readable storage medium and a computer program mechanism embedded therein, wherein the computer program mechanism includes: instructions for providing a description of a view of a dataset that includes multiple fields associated with the dataset; instructions for determining a set of properties for each of the multiple fields;

and instructions for automatically translating the description into one or more models based on the respective properties of the multiple fields and a set of predefined heuristics.

BRIEF DESCRIPTION OF THE DRAWINGS

FIG. 1 is a prior art screenshot displaying a portion of a commercial dataset related to the sales and marketing activities of a soft drink company using Microsoft Excel.

Like reference numerals refer to corresponding parts throughout the several views of the drawings.

DETAILED DESCRIPTION OF THE INVENTION

The present invention provides methods, computer program products, and computer systems for automatically generating and displaying models derived from a multi-dimensional dataset. In a typical embodiment, the present invention builds and displays a view of the dataset based on a user specification of the view. Based on the user specification, the present invention calculates parameters of one or more model formulas associated with the dataset. The model formulas are automatically presented to the user together with the view of the dataset.

The present invention operates on a set of tuples, commonly referred to as a multi-dimensional dataset. As one skilled in the art will realize, the dataset can be a relational database, a multi-dimensional database, a semantic abstraction of a relational database, or an aggregated or unaggregated subset of a relational database, multi-dimensional database, or semantic abstraction. Fields are categorizations of data in a dataset. A tuple is an entry of data (such as a record) in the dataset, specified by properties from fields in the dataset. A search query across the dataset returns one or more tuples.

A view is a visual representation of a dataset or a transformation of that dataset. Text tables, bar charts, line graphs, and scatter plots are all examples of types of views. Views contain marks that represent one or more tuples of a dataset. In other words, marks are visual representations of tuples in a view. A mark is typically associated with a type of graphical display. Some examples of views and their associated marks are as follows:

| View Type | Associated Mark |
| --- | --- |
| Table | Text |
| Scatter Plot | Shape |
| Bar Chart | Bar |
| Gantt Plot | Bar |
| Line Graph | Line Segment |
| Circle Graph | Circle |

Figure 2:
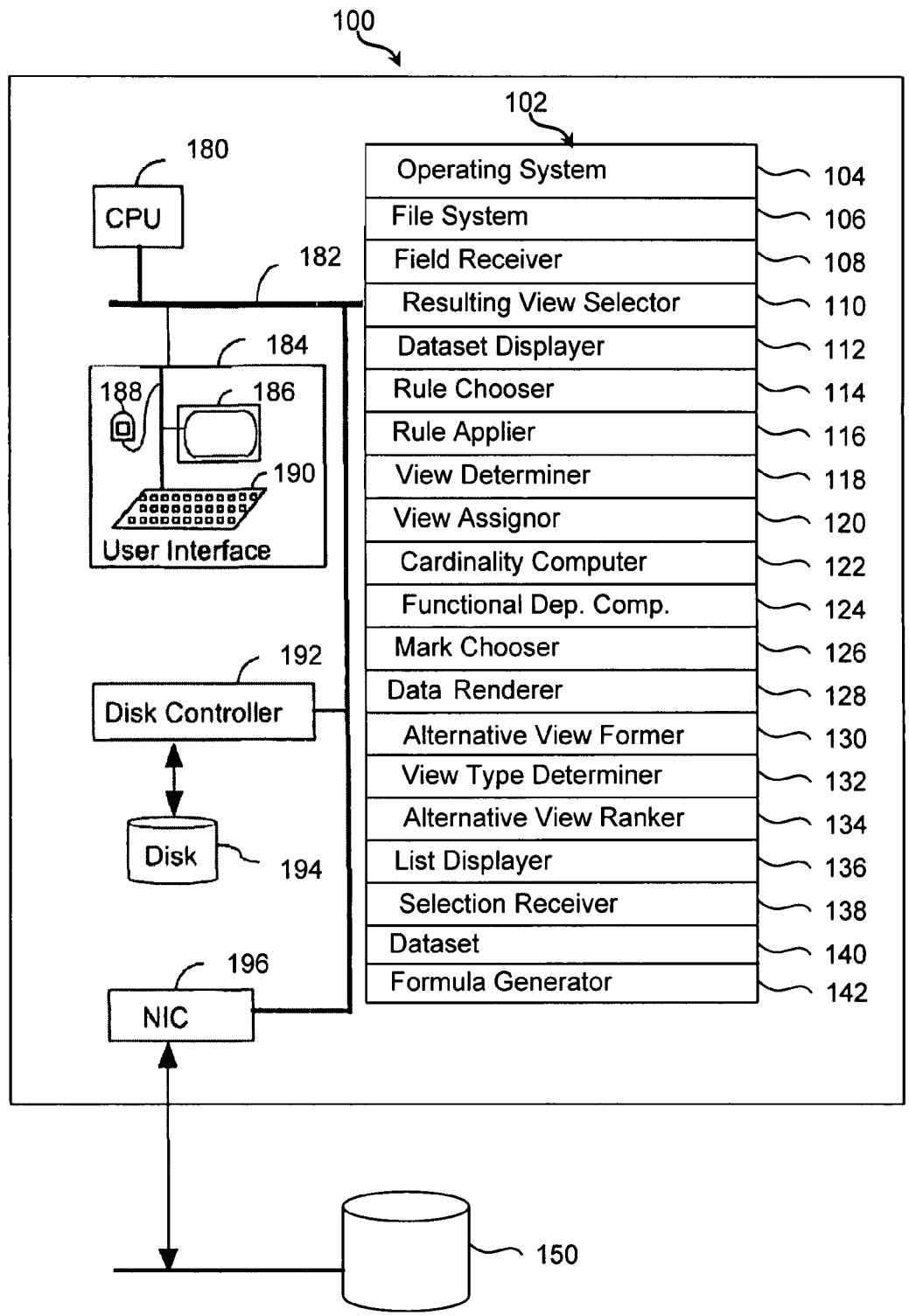
FIG. 2 is a block diagram illustrating a computer system that facilitates the visualization of a dataset in accordance with some embodiments of the present invention.

FIG. 2 is a block diagram illustrating a computer system that facilitates the visualization of a dataset in accordance with some embodiments of the present invention. The system 100 includes a memory 102, CPU 180, user interface 184, storage unit 194, disk controller 192, and a bus 182 that "enables communication along" all of the system's elements. The system 100 may also have a network interface card (NIC) 196 to enable communication with other systems on a different network. The memory 102 stores an operating system 104, and a file system 106, as well as various modules related to the present invention. Additionally, the memory 102 may also store a multi-dimensional dataset 140, which contains tuples. The system 100 may also be connected to database 150 where a dataset may be retrieved and stored in the memory 102. The memory 102 also stores computer program mechanisms that are necessary to some embodiments of the present invention.

Figure 3A:
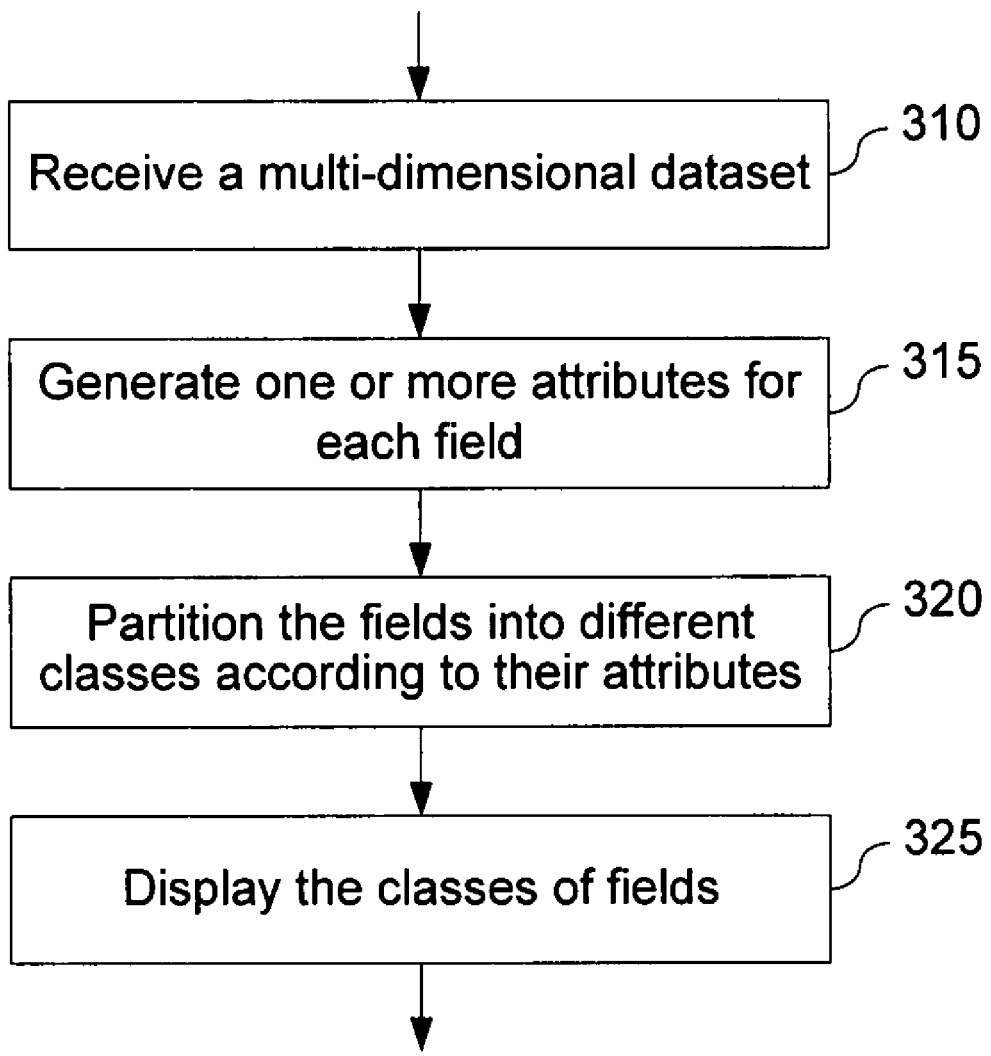
FIG. 3A is a flowchart illustrating a process of loading a dataset into the computer system in accordance with some embodiments of the present invention.

FIG. 3A is a flowchart illustrating a process of loading a multi-dimensional dataset into a computer system in accordance with some embodiments of the present invention. At step 310, the computer system receives a multi-dimensional dataset. This dataset is specified by a user through a graphical user interface to the computer system. In some embodiments, the dataset stored on the same computer system. The computer system can access the dataset through the disk controller. In some other embodiments, the dataset is located in a remote database connected to the computer system through a network. The computer system can retrieve the dataset from the database by submitting queries to the database.

Figure 1:
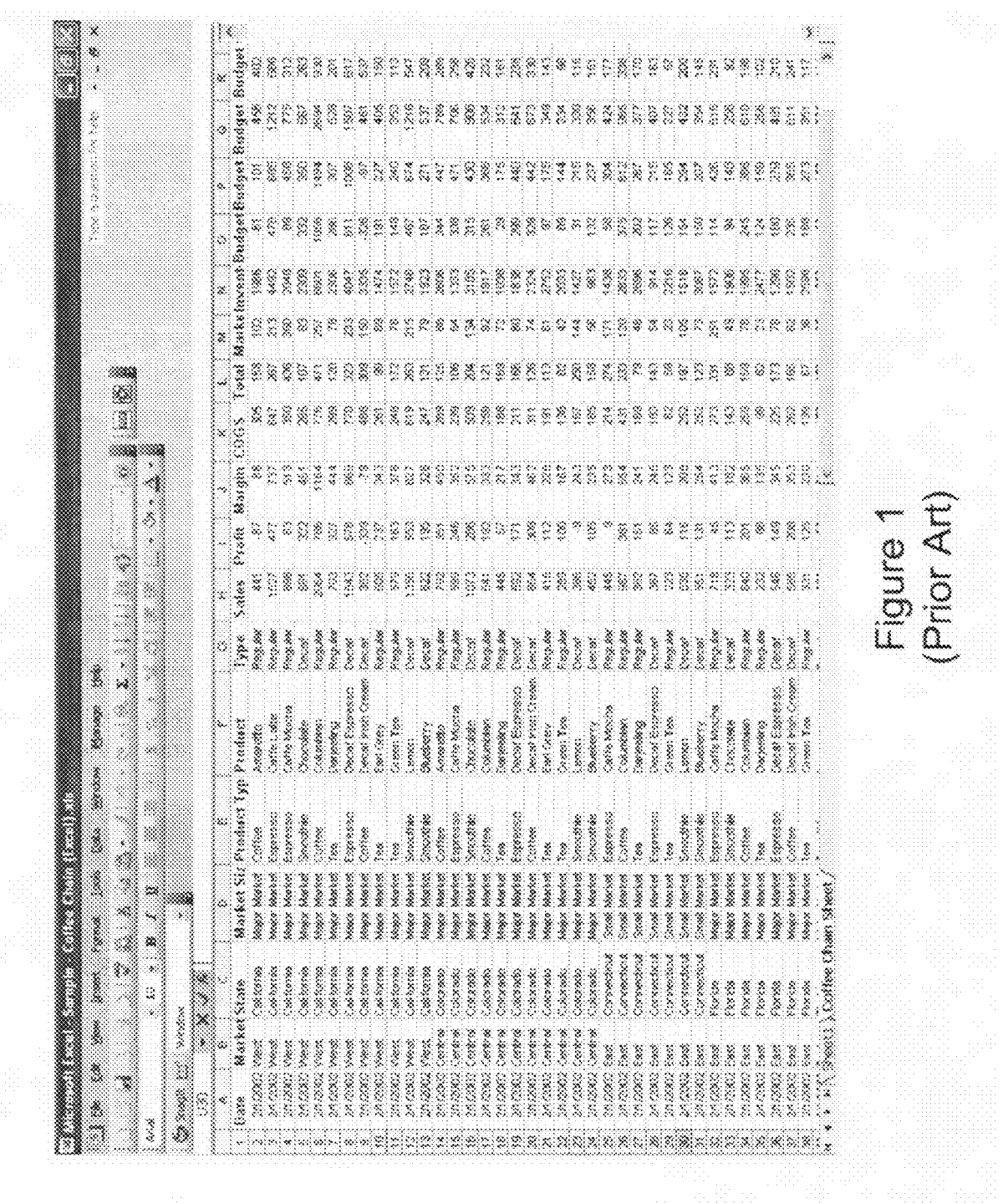

At step 315, the computer system generates one or more properties for each field of the dataset. One of the properties is a field type. Generally speaking, the fields of a dataset have one of two field types, "categorical" or "quantitative". A categorical field is one whose domain is an enumerable set of values. For example, the "State" field in the spreadsheet of FIG. 1 is a categorical field. The "State" field has only 50 possible values because there are only 50 states in the United States. Different values like "California", "Colorado", and "Florida" correspond to different geographical regions. For convenience, these values are often displayed in alphabetical order. In contrast, the "Date" field takes on a set of enumerable values in terms of year, quarter, or month, etc. Unlike the "State" field, the values corresponding to the "Date" field have a quantitative interpretation. For example, April, 2006 is obviously after March, 2006, but before May, 2006. In other words, the values corresponding to the "Date" field are ordinal.

In contrast, the value of a quantitative field is always ordinal, which may be continuous or discrete. For example, the "Sales" field in the spreadsheet has values such as "441", "681", and "382." Although they are not displayed in an increasing or decreasing order in the table, the value "441" is clearly larger than the value "382" and smaller than the value "681." Moreover, the possible value of a quantitative field is usually continuous, not discrete. For example, the value of the "Sales" field can be any real number from zero to infinity. As will become apparent below, this dichotomy of fields into categorical and quantitative types is important when the computer system subsequently generates models for the dataset in accordance with the present invention.

At step 320, based on the properties associated with different fields, the computer system partitions all the fields into two classes, "dimension" and "measure." A field in the dimension class is one to which some aggregate operations (e.g., sum or average) have not been applied. On the other hand, a field in the measure class is one whose values can be summed or averaged and produce a meaningful result. For example, the sum (or average) of the values in the "Sales" field provides the total (or average) sales revenue within a specified time period.

Although quantitative fields are often in the measure class and categorical fields are usually in the dimension class, there are exceptions. For example, the fields related to the longitude and latitude of a geographical location are quantitative fields since their values are continuous. But there is no reasonable interpretation of the sum of the values in these fields.

The class affiliation of a field often provides hints on what type of role the field plays in the description of a view of the dataset. For example, the "Sales" field is in the measure class. Its value depends upon the value in the "State" field, the value in the "Product" field and the value in the "Date" field. Different products sold in different states at different times may have different sales revenues. In contrast, the "State" field is in the dimension class. Its value is not apparently dependent upon any other field's value. But in some embodiments, there can be a relationship between one categorical field (e.g., "Product") and another one (e.g., "Product Type") although this relationship is hard to describe using a mathematical formula. This difference between the dimension class and the measure class is used by the computer system when generating model formulas from the dataset.

At step 325, the computer system displays the dimension and measure classes of fields. The fields in the dimension class are usually categorical fields to which some aggregate operations (e.g., sum or average) are not applicable. The fields in the measure class are often quantitative fields whose values can be summed or averaged together. For example, the sum (or average) of the values in the "Sales" field provides the total (or average) sales revenue. The two classes of fields are used by a user subsequently to formulate different descriptions of the dataset. Based on the descriptions, the computer system generates and displays different views of the dataset. These descriptions are also used for generating models corresponding to the different views.

Figure 3B:
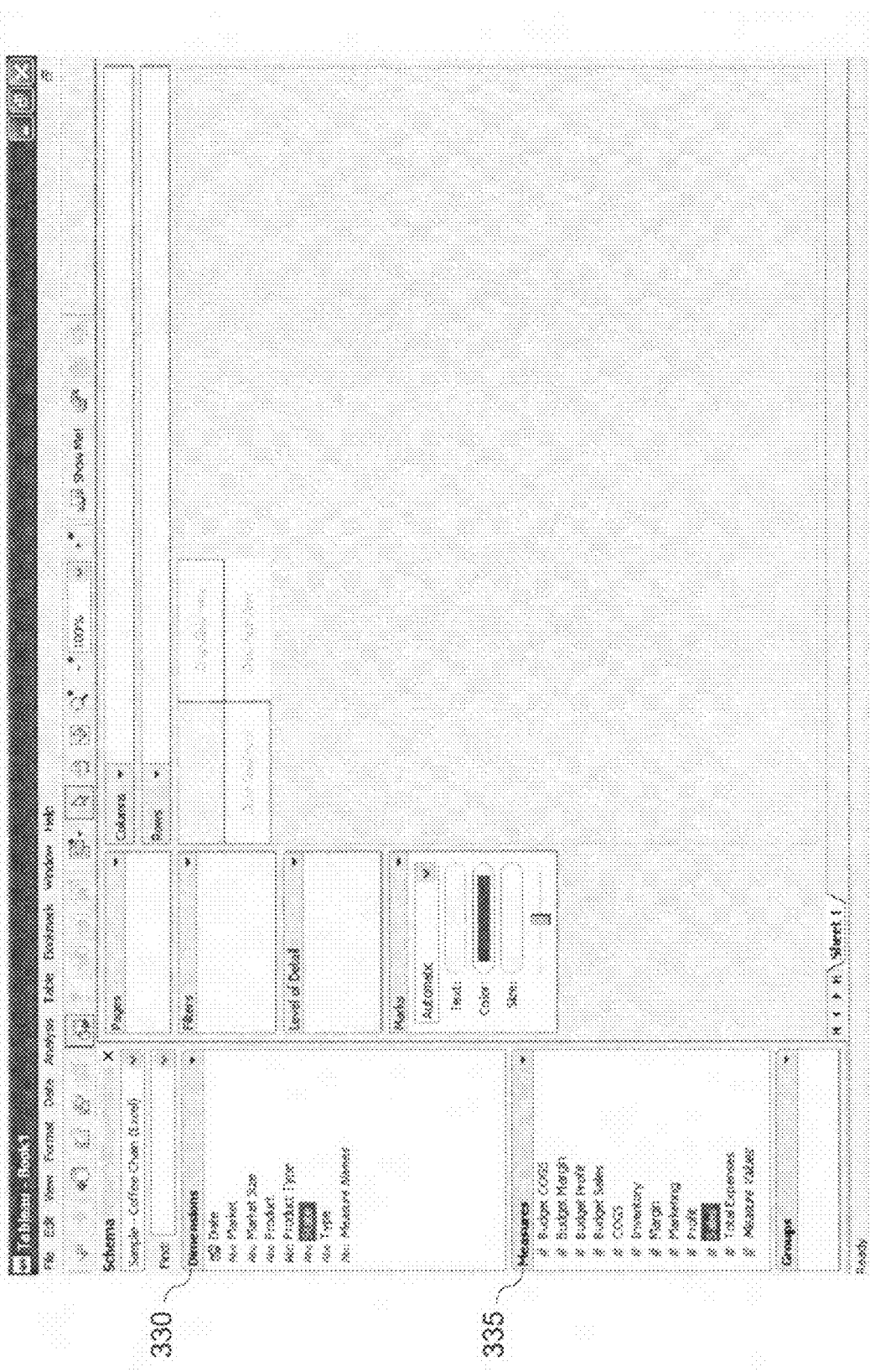
FIG. 3B is an exemplary screenshot displaying the dataset loaded into the computer system in accordance with some embodiments of the present invention.

FIG. 3B is an exemplary screenshot displaying the dataset after it is loaded into the computer system in accordance with some embodiments of the present invention. On the left of the screenshot are two classes of fields, the "Dimensions" class 330 and the "Measures" class 335. In this example, all the fields in the class 330 are categorical fields such as "Date", "Market", "State", etc. All the fields in the class 335 are quantitative fields such as "Budget Margin", "Inventory", "Sales", etc. To the right of the two classes is a region for a user to generate a description of a desired view of the dataset and the view itself.

Figure 4A:
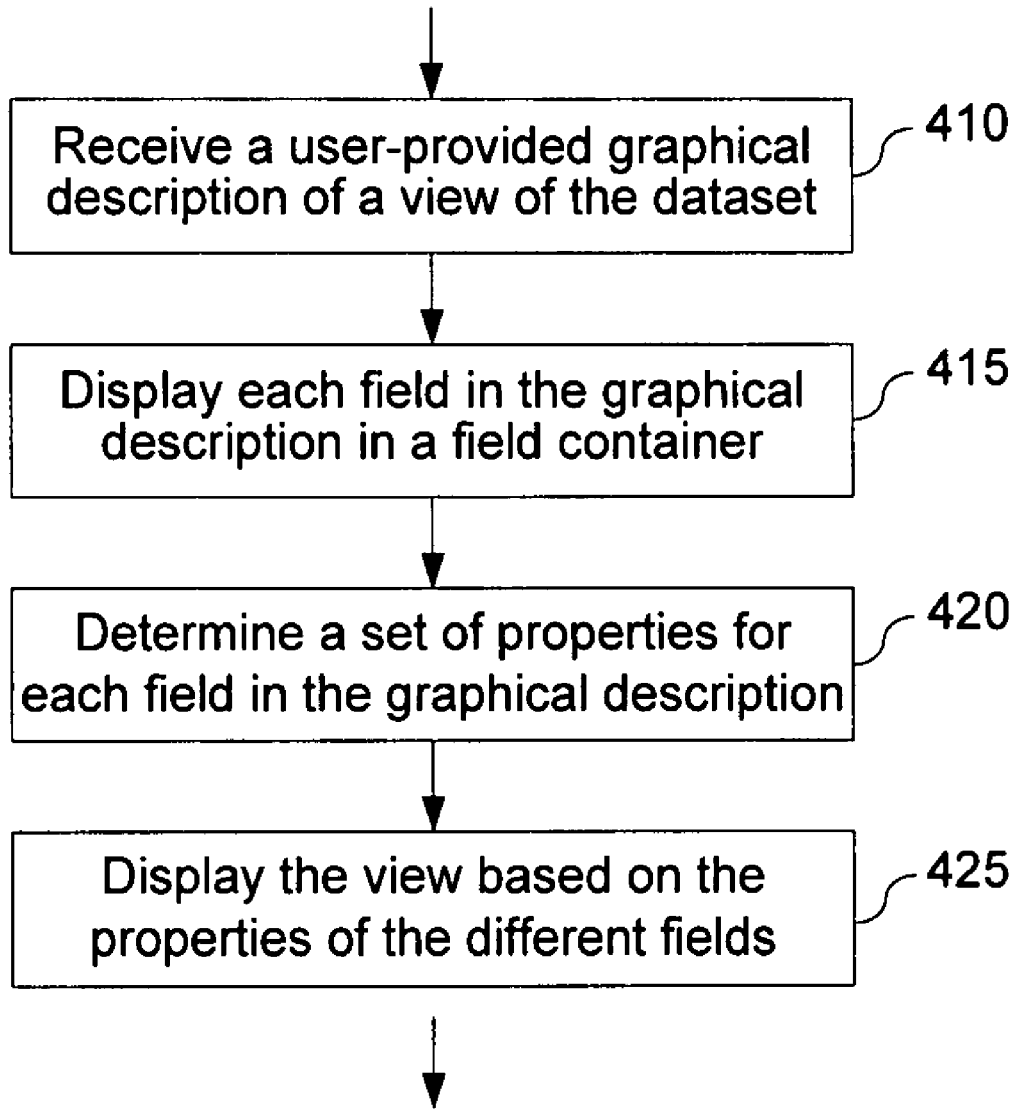
FIG. 4A is a flowchart illustrating a process of displaying a view of the dataset in accordance with some embodiments of the present invention.

FIG. 4A is a flowchart illustrating a process of displaying a view of the dataset based on a user-provided description in accordance with some embodiments of the present invention. As shown in FIG. 3B, the two classes of fields are displayed to a user of the computer system. In order to visualize the dataset, the user needs to provide a description of a view of the dataset. This description usually corresponds to the user's specific interest in a particular aspect of the dataset.

For example, presume that a user is interested in visualizing the total sales revenues for different states. A conventional approach to this problem requires that the user express his or her interest as a simple query using the structured query language (SQL):

SELECT State, SUM(Sales)
FROM Dataset
GROUP BY State;

The text result of executing the SQL query against the dataset is shown in the table below. A significant problem with this conventional approach is that a user must know how to express the user's interests using SQL.

| State | SUM(Sales) |
|---|---|
| California | 310278 |
| Colorado | 151505 |
| Connecticut | 80953 |
| Florida | 119936 |
| Illinois | 223079 |
| Iowa | 175755 |
| Louisiana | 73747 |
| Massachusetts | 96949 |
| Missouri | 79414 |
| Nevada | 190453 |
| New Hampshire | 47792 |
| New Mexico | 50668 |
| New York | 223809 |
| Ohio | 109006 |
| Oklahoma | 88487 |
| Oregon | 130802 |
| Texas | 119079 |
| Utah | 112610 |
| Washington | 123825 |
| Wisconsin | 106087 |

Of course, this problem is more challenging as in many cases, a business-wise intuitive user's interest/hypothesis may correspond to a very complicated SQL query. Therefore, users with little or no SQL knowledge find it difficult to explore datasets using SQL queries. They have a strong need to express their interests in a way that is understood by both the users themselves and the computer system.

Figure 4B:
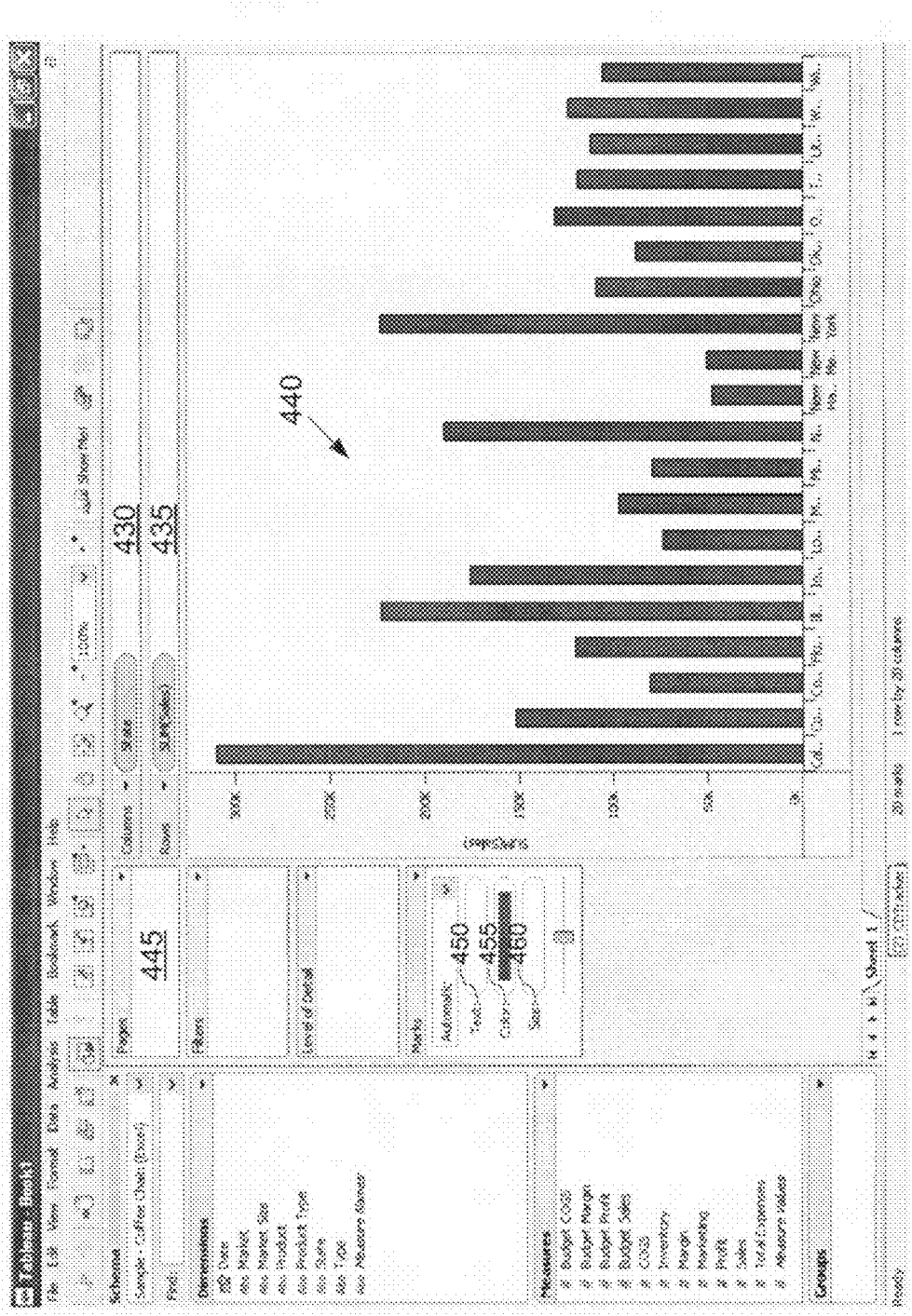
FIG. 4B is an exemplary screenshot displaying a view of the dataset in accordance with some embodiments of the present invention.

FIG. 4B is an exemplary screenshot displaying a description and a view of the dataset in accordance with some embodiments of the present invention. At step 410, instead of an SQL query, a user characterizes his or her interest using a description corresponding to a view of the dataset. Using the same example, the user is interested in visualizing the total sales revenues for different states. Therefore, the description should include the "State" and "Sales" fields of the dataset. Intuitively, this interest can be formulated into a 2-D diagram. The horizontal axis of the 2-D diagram corresponds to the value in the "State" field of the dataset. The vertical axis corresponds to the sum of the value in the "Sales" field of the dataset and the total sales revenues for different states can be represented using a bar chart. In other words, the description associates the "State" and "Sales" fields with the horizontal and vertical axes of the 2-D diagram, respectively.

At step 415, the computer system displays each field in the description in a specific field container. Accordingly, the "State" field is displayed in a "Column" field container 430 and the "SUM(Sales)" field is displayed in a "Row" field container 435. At step 420, the computer system determines a set of properties for each field in the description. The computer system uses the properties of the different fields to configure the view associated with the description. In this example, since the "SUM(Sales)" field is a quantitative field from the measure class, the description, by default, automatically instructs the computer system to calculate the sum of the values in the "SUM(Sales)" field, each sum corresponding to one state. The "State" field is a categorical field from the dimension class. There is no need to automatically aggregate the values in this field. The properties of the different fields in a description are also used by the computer system to generate one or more model formulas for the data view associated with the description. Based on their respective properties, the computer system determines which fields are the independent variables of the model formulas, which are the dependent variables and which should be considered as additional factors. In some embodiments, the computer system makes these decisions using a set of heuristics. A more detailed discussion of these heuristics is provided below in connection with FIGS. 6A through 6Q.

At step 425, the computer system displays a view of the dataset based on the description. As shown in FIG. 4B, the resulting bar chart 440 is a graphical visualization of the table listing the total sales revenues for different states in the alphabetical order. After a simple glance at the view, the user can easily tell that California has the largest total sales revenue and New Hampshire has the lowest within a specified time period (from 2002 to 2003). The total sales revenue of a particular state encompasses the sales of all different types of products at the state during the two years. A more detailed description of visualizing a dataset based on a user-provided description can be found in U.S. patent application Ser. No. 11/223,658, "Computer Systems and Methods for Automatically Viewing Multidimensional Databases", which is incorporated herewith in its entirety for reference.

Very often, a user's interest is much more complicated than the one discussed above and involves more than two fields. This user interest may have to be translated into a multi-dimensional view of the dataset. To support this multi-dimensional view, the computer system provides more than two field containers to host different fields. For example, the user may be interested in visualizing the total sales revenues for different states for different years (e.g., 2002 and 2003). This requirement inevitably involves the "Date" field. To do so, the user can augment the current description by dropping the "Date" field into the "Pages" field container 445. By default, the computer system separates sales data associated with Year 2002 from sales data associated with Year 2003. For each year, the computer system generates a separate bar chart. The user can view each individual bar chart to see the sales records for different states for each year. FIG. 4B depicts additional encoding field containers such as the "Text" 450, the "Color" 455, and the "Size" 460. A more detailed discussion of these field containers is provided below in connection with FIGS. 6A through 6Q.

In some embodiments, visualization of a dataset as shown in FIG. 4B is not enough. For example, a user may be interested in making forecasts from the existing data. Making a prediction from known information is a modeling process. Such a process generates an analytical formula for the dataset or a subset. For convenience, the two terms, model and analytical formula (or formula), are used interchangeably in this specification. An analytical formula usually has multiple parameters and the values of the parameters are determined from the existing data values in the dataset using tools such as statistical modeling. Statistical modeling is a well-known method for simplifying descriptions or interpretations of data using statistical models. The statistical models are constructed from some mathematically or numerically defined relationships. A more detailed description of statistical modeling can be found in "Statistical Models in S" (edited by John M. Chambers and Trevor J. Hastie), Chapman & Hall/CRC (1991), which is incorporated herewith in its entirety for reference.

Figure 5A:
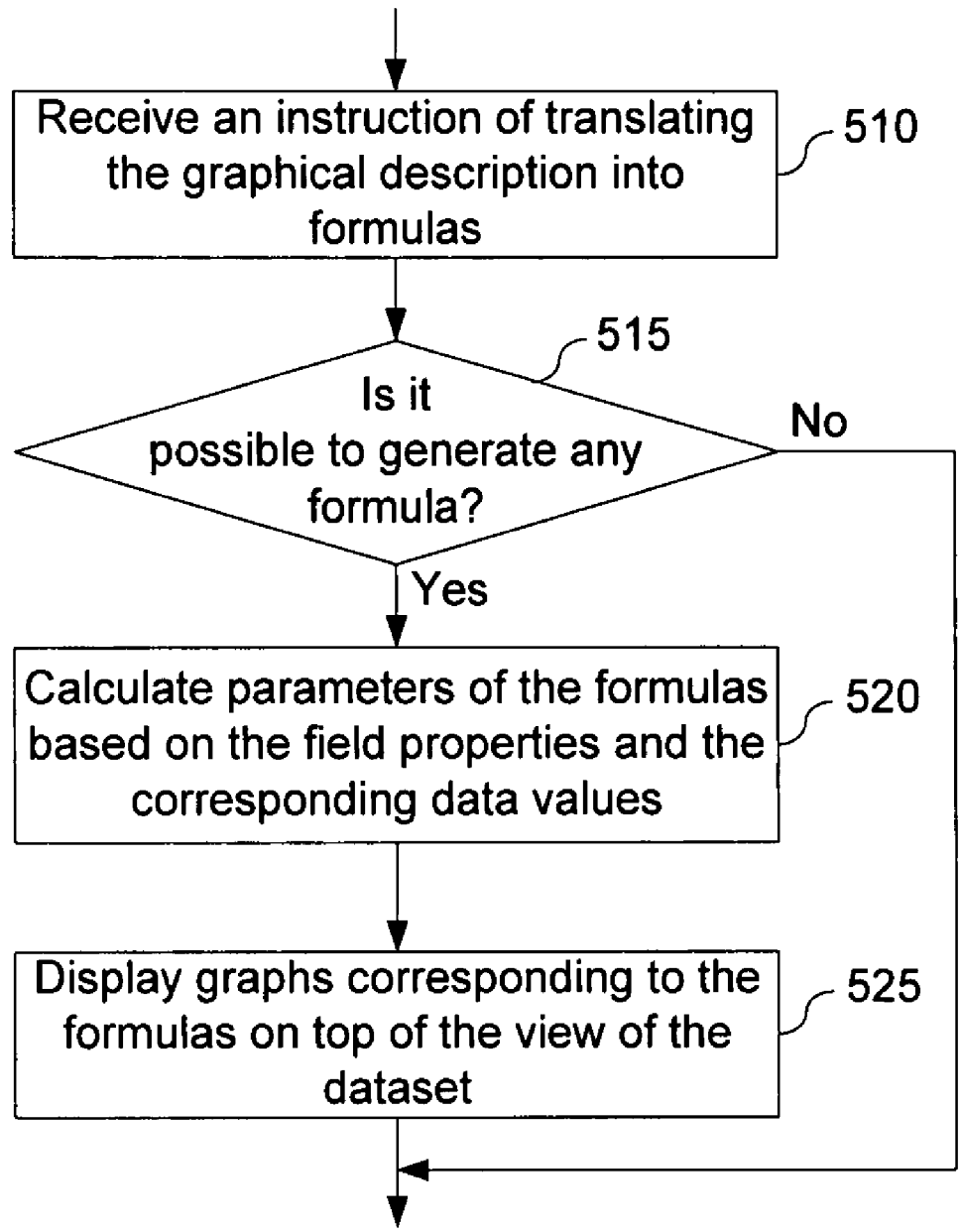
FIG. 5A is a flowchart illustrating a process of generating and displaying a model of the dataset in accordance with some embodiments of the present invention.

FIG. 5A is a flowchart illustrating a process of generating and displaying a model of the dataset in accordance with some embodiments of the present invention. At step 510, the computer system receives an instruction from the user to translate the description into a model formula for the current data view on display. After getting the instruction at step 515, the computer system determines if it is possible to translate the description into any model formula. The computer system makes this determination by examining the properties of the fields involved in the current view and their respective properties in the view.

Sometimes, it may be impossible or meaningless to derive a model formula from a description. The description shown in FIG. 4B is such an example. As noted above, the description has two fields, "Sales" and "State." Although the bar chart organizes the states in the alphabetical order, the "State" field is a categorical field and its values are not ordinal per se. For example, it is impossible to predict the total sales revenue at a state not listed in the table, e.g., Alaska, from the existing data. The total sales revenue at Philadelphia may be correlated with its population size. But it has nothing to do with the state name "Philadelphia." As a result, the computer system terminates the process by skipping steps 520 and 525.

Figure 5B:
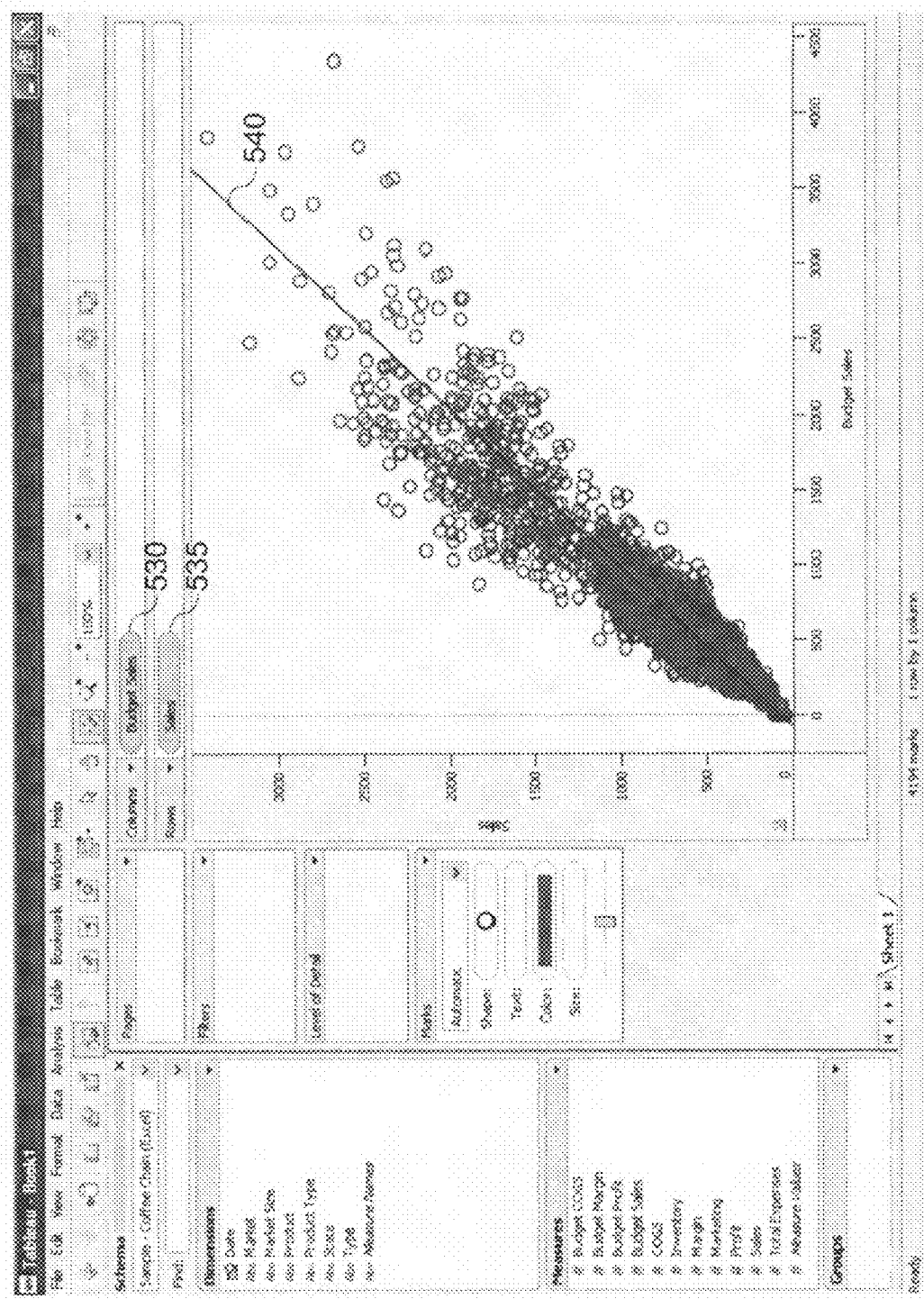
FIG. 5B is an exemplary screenshot of a view and its associated model of the dataset in accordance with some embodiments of the present invention.

In many other cases, it is possible to translate a description into an analytical model formula that makes business sense. FIG. 5B depicts another description and its associated view. In this example, it is the "Budget Sales" field, not the "State" field, in the "Column" field container, and the "Sales" column remains in the "Row" field container. A correlation of the values in the two fields indicates the accuracy of the prediction of the sales revenue from the budget sales revenue.

In some embodiments, the description is not generated by a user dragging and dropping different fields into respective field containers. Rather, the user may generate a text string, e.g., using extensible markup language (XML). The text string includes instructions of associating different fields with respective field containers. The computer system generates the models by interpreting the text string.

At step 520, the computer system calculates the parameters of a model formula simulating the correlation of the two fields. Ideally, the actual sales revenue should be equal to the budget sales revenue. In this example, the computer system simulates this linear relationship with a model formula:

$$y=ax+b,$$

where x represents the budget sales revenue and y represents the actual sales revenue, and a and b are coefficients that can be determined from the dataset using statistical methods.

Using the corresponding values in the dataset, the computer system calculates the parameters a and b. As a result, they are, respectively, $$a=0.945,$$

$$b=77.1.$$

Clearly, the actual sales revenue is about 95% of the budget sales revenue. In other words, the predicted value is slightly higher than the actual outcome. As step 525, the computer system displays the graph 540 of the simulated relationship, y=0.945x+77.1, on top of the view of the dataset. A more details discussion of the process of generating various analytical models from a dataset is provided below.

The computer system used to perform these embodiments of the present invention is shown in FIG. 2. In particular, the field receiver 108 performs step 410 by receiving fields selected by the user. The resulting view selector 110 performs step 420 and selects a resulting view. The dataset displayer 112 performs step 425 and displays the dataset according to the resulting view.

According to one embodiment of the invention, the resulting view selector 110 selects the resulting view by choosing rule(s) for the user selected fields. This is accomplished by the rule chooser 114. The rule applier 116 then applies the rule(s) to determine the resulting view's view type. In another embodiment of the invention, before the rule chooser 114 chooses rule(s), the view determiner 118 determines whether there is any view corresponding to the user selected fields or the description. In yet another embodiment of the invention, the dataset is displayed in when the mark chooser 126 chooses a mark for the resulting view, and the dataset renderer 128 renders the dataset according to the mark.

As noted above, there may be some inherent relationships between different fields of a description. For example, the fields in the "Row" container may be dependent upon the fields in the "Column" container. This relationship is often embedded in the dataset or a subset thereof. Sometimes, the relationship may have an analytical expression. The analytical expression and its graphical counterpart provide a user with more insight into the dataset. Accordingly, the computer system can generate model formulas simulating the relationships between different fields of the description using the underlying dataset. On the other hand, not every relationship between a column field and a row field of the description has an analytical expression that makes sense to the user. The description shown in FIG. 4B is one of the examples. In some other embodiments, the computer system may assign a quantitative interpretation (e.g., a digital value) to each state shown in the figure and then generate an analytical expression accordingly from different states.

The present invention describes a set of heuristics. This set of heuristics is used for interpreting various descriptions of datasets. In particular, when a user provides a description of a dataset to the computer system, the computer system applies the set of heuristics to the description and selects appropriate fields from the description to generate different model formulas for the selected fields. These heuristic-based model formulas may reveal the inherent relationships between the different fields of the description and therefore give the user more insight into the dataset.

In some embodiments, a generic model formula can be expressed in the following format:

$$y = M_1 op\ M_2 op\ \ldots\ op M_N op\ f(x),$$

where the terms x and y are the independent and response variables of the formula, and some of the parameters $M_1$, $M_2$, ..., $M_N$ are the factors of the formula. The operator op determines whether the two operands on both sides of the operator interact. The expression f(x) may take on one of many known model types including linear, polynomial, exponential, logarithmic, transcendental, and other mathematical functions. Each model type has one or more coefficients. These coefficients are determined by the computer system using data selected from a dataset. The variables and factors correspond to different fields in a user-provided description of a view of the dataset. The data values associated with the independent and response variables are directly involved in the computation of the coefficients.

The generic expression of the coefficients of a model can be expressed as follows:

$$y = Dc,$$

where y is a vector containing the values of the response variable, D is a design matrix, and c is the set of coefficients of the model to be generated. The elements of the design matrix D depend on the values of the factors and the independent variables. The solution to coefficient set c can be expressed as:

$$c = (D^T D)^{-1} D^T y,$$

where $D^T$ is the transpose of the matrix D and $(D^T D)^{-1}$ is the inverse of the square matrix $(D^T D)$.

For illustrative purposes, assume that the computer system simulates the relationship between the independent variable x and the response variable y using a quadratic equation. It will be apparent to one skilled in the art that the methodology discussed below can be easily applied to other types of models.

In particular, this quadratic equation can be expressed as:

$$y = M(ax^2 + bx + c),$$

where a, b, c are the coefficients of the quadratic equation and M is a categorical factor that has three possible values u, v, and w. In this example, every categorical value u, v, or w is associated with a unique set of coefficients $a_i$, $b_i$, and $c_i$ or $$(M=u) \sim (a_1, b_1, c_1),$$

$$(M=v) \sim (a_2, b_2, c_2),$$

$$(M=w) \sim (a_3, b_3, c_3).$$

The table below lists the N tuples derived from the dataset, which will be used to determined the three sets of coefficients $a_i$, $b_i$, and $c_i$:

| y | M = u | M = v | M = w | x |
|---|---|---|---|---|
| $y_1$ | 1 | 0 | 0 | $x_1$ |
| $y_2$ | 0 | 1 | 0 | $x_2$ |
| ... | ... | ... | ... | ... |
| $y_N$ | 0 | 0 | 1 | $x_N$ |

Based on the N tuples, the generic expression of the coefficients can be expressed as:

$$\begin{bmatrix} y_1 \\ y_2 \\ \ldots \\ y_N \end{bmatrix} = \begin{bmatrix} x_1^2 & 0 & 0 & x_1 & 0 & 0 & 1 & 0 & 0 \\ 0 & x_2^2 & 0 & 0 & x_2 & 0 & 0 & 1 & 0 \\ \ldots & \ldots & \ldots & \ldots & \ldots & \ldots & \ldots & \ldots & \ldots \\ 0 & 0 & x_N^2 & 0 & 0 & x_N & 0 & 0 & 1 \end{bmatrix} \begin{bmatrix} a_1 \\ a_2 \\ a_3 \\ b_1 \\ b_2 \\ b_3 \\ c_1 \\ c_2 \\ c_3 \end{bmatrix}$$

As noted above, the user provides a description of the view by dragging and dropping fields from the two classes into different field containers. The computer system then automatically transforms this description into model formulas. A key part of this transformation process is deciding which fields become the categorical factors in the model formulas and which fields become the independent and response variables.

The principle of transforming a user-provided description into a model formula is to select two fields from the description, which may be potentially related, as the independent and response variables of the model formula, respectively, and treat the remaining categorical fields in the description as factors of the model formula. This transformation should match the user's expectation of examining whether and how the responsible variable field is dependent upon the independent variable field and whether and how the different factors affect this dependency relationship.

In some embodiments, this general criterion can be fine tuned into a set of heuristics as follows:

Rule One: Determination of the response and independent variables:
  If there is only one quantitative field in either the row or column field containers, it is the response variable of the formula.
  If there are quantitative fields in both the row and column field containers, the quantitative field from the dimension class is the independent variable and the remaining quantitative field is the response variable.
    If both the quantitative fields are from the dimension class, the quantitative field in the row field container is the response variable.
    If neither of the quantitative fields is from the dimension class, the quantitative field in the row field container is the response variable.
  The field chosen as the independent variable must have a quantitative interpretation.

Rule Two: Categorical fields in the row, column, and pages field containers are factors in the model formula if they are not the independent variables of the model formula.

Rule Three. Categorical fields in any encoding field containers are factors in the model formula if there are more than one data points corresponding to each value in the categorical fields.

Rule Four: If there are multiple quantitative fields in the row or column field containers, the computer system generates multiple model formulas.

Rule Five: Quantitative fields in any encoding field containers are not factors in the model formula.

Rule Six: Missing values from the domain of a categorical independent variable of a model formula are added.

Figure 6A:
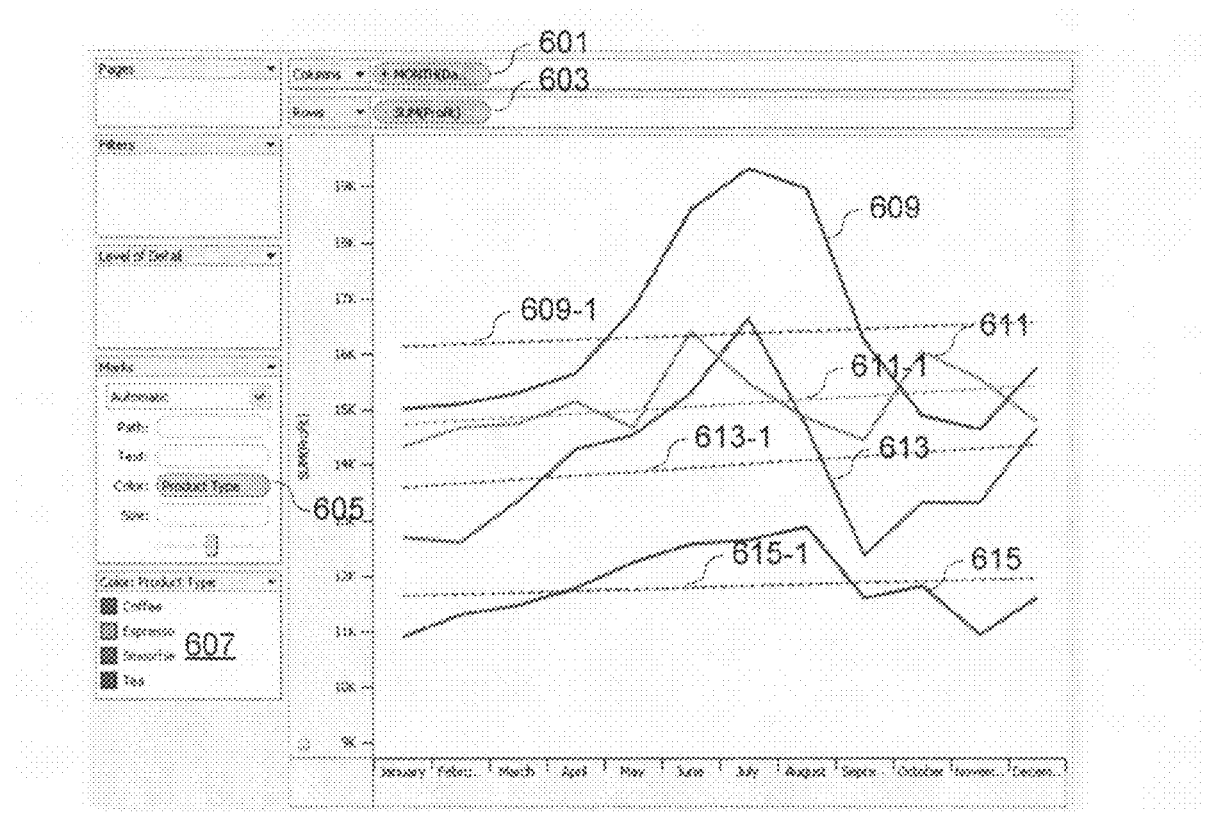
FIGS. 6A through 6Q are exemplary screenshots of different views of the dataset in accordance with some embodiments of the present invention.
Figure 6B:
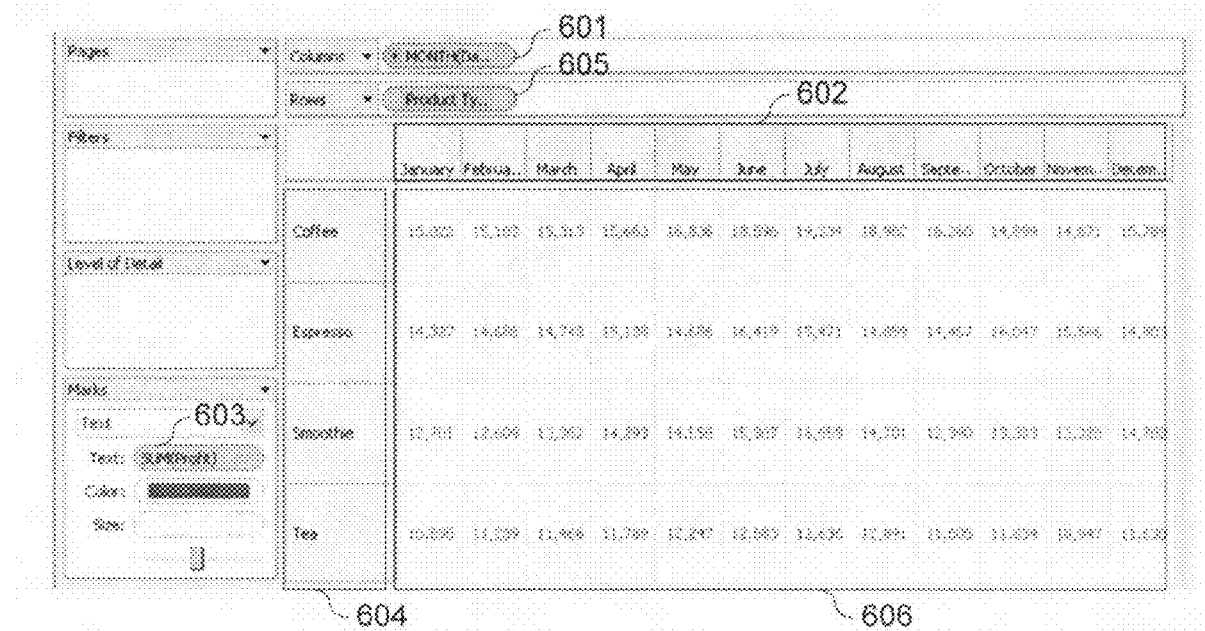
Figure 6C:
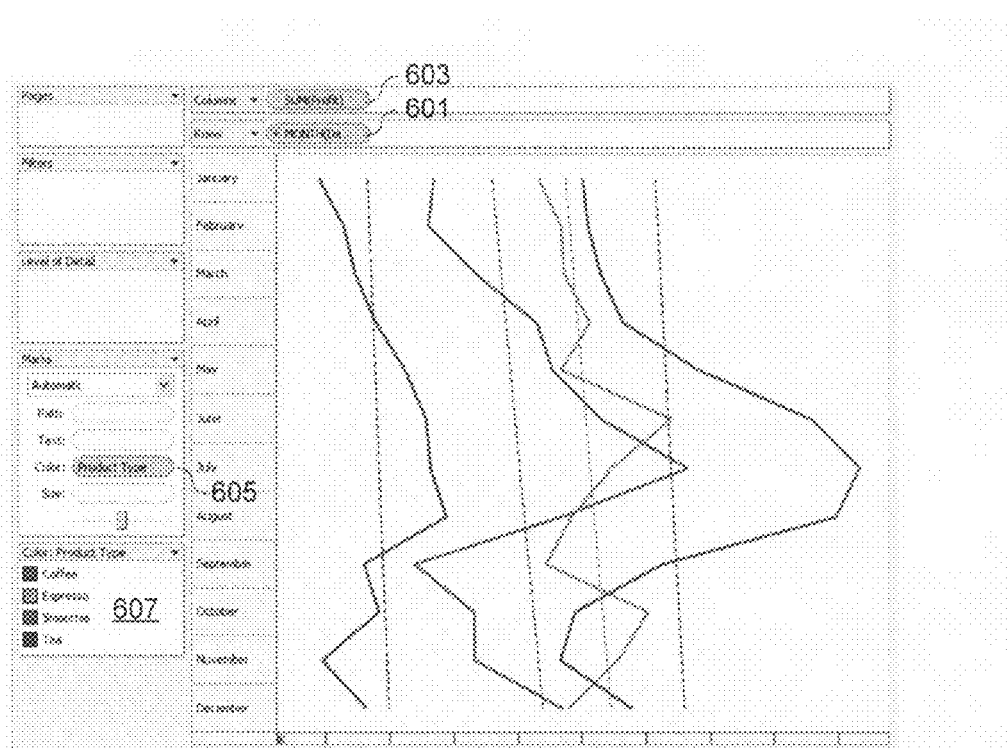
Figure 6D:
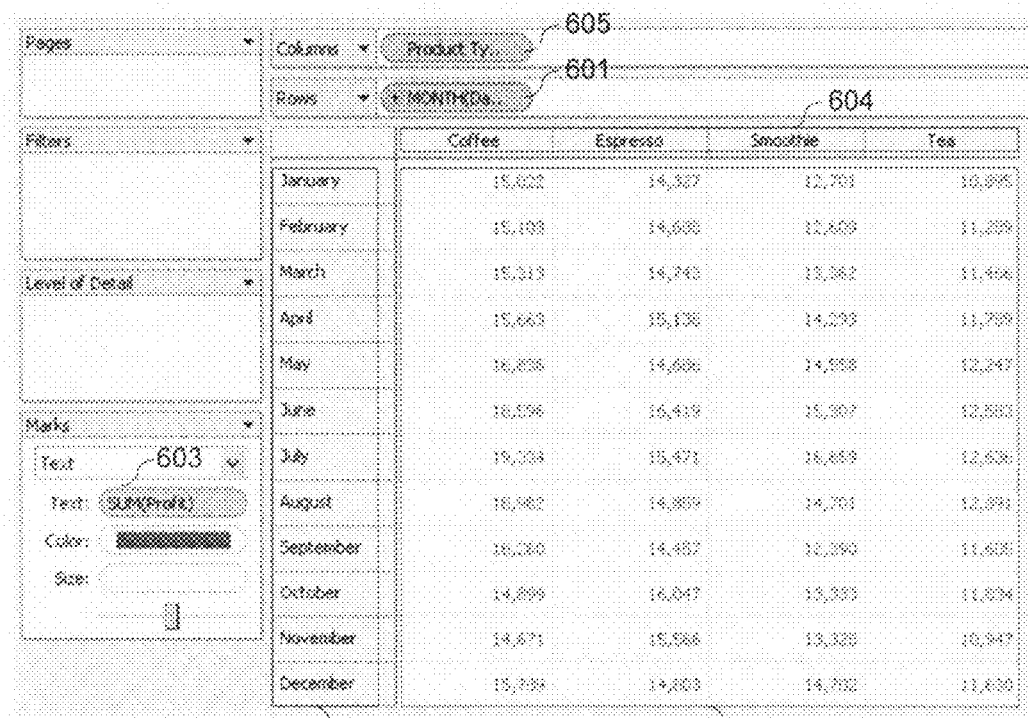
Figure 6E:
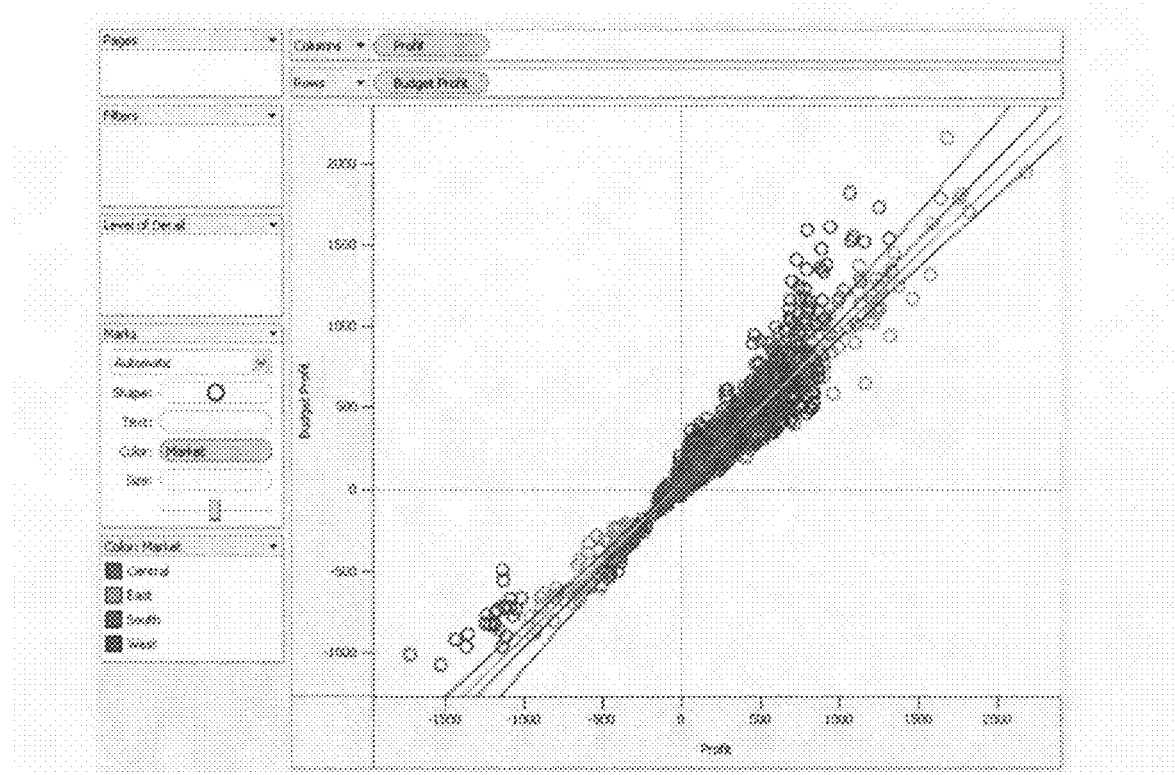
Figure 6F:
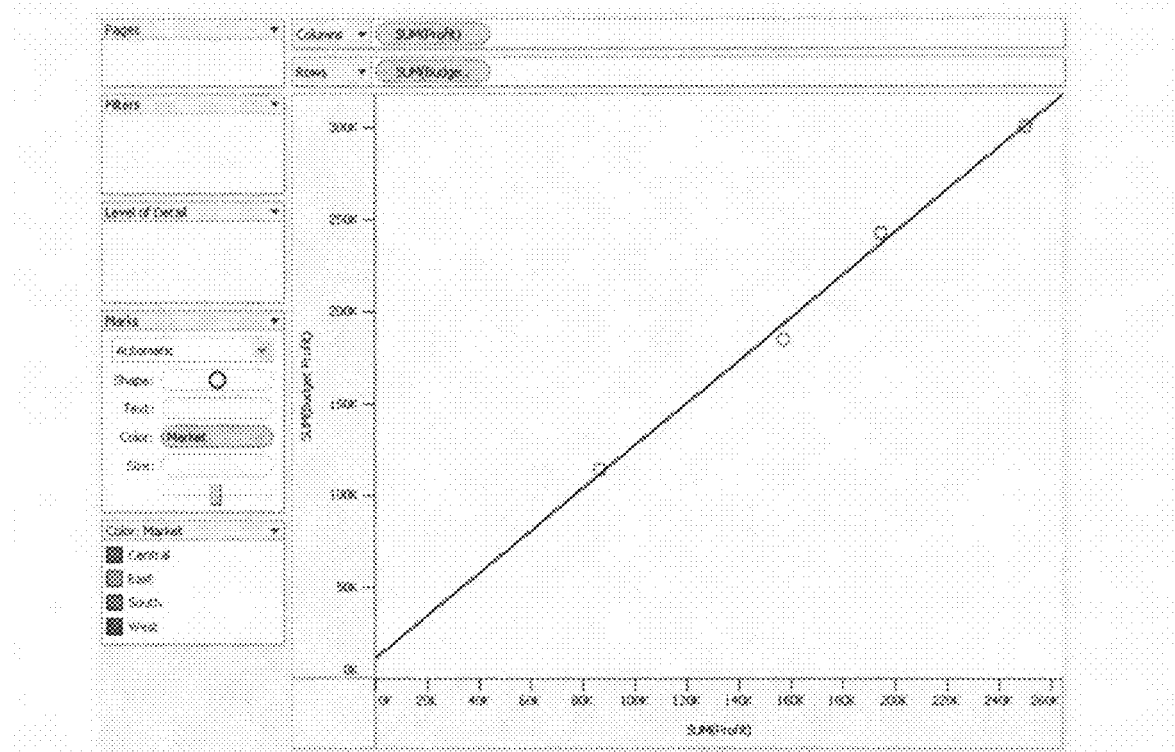
Figure 6G:
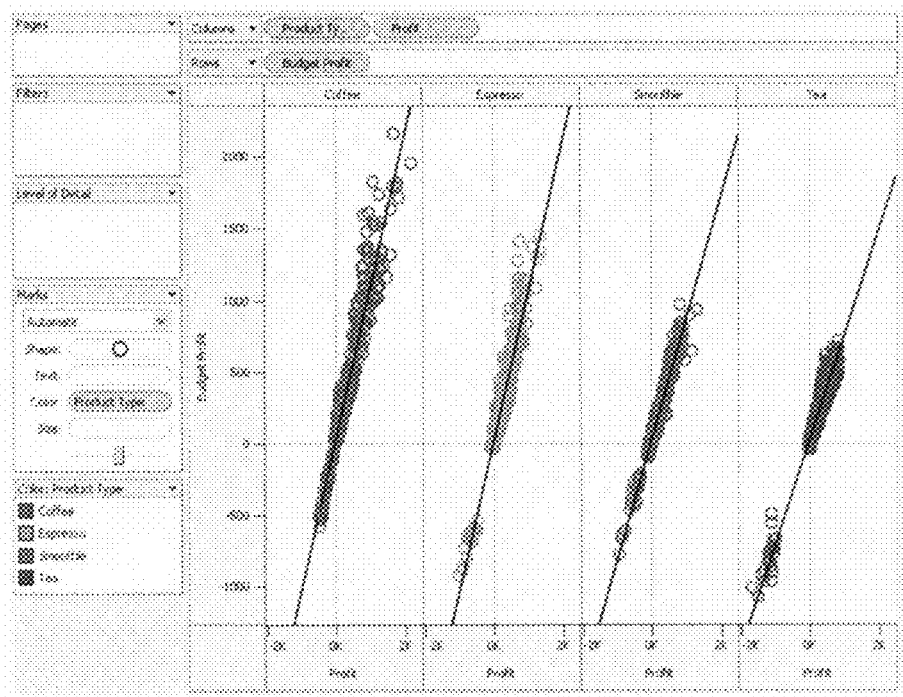
Figure 6H:
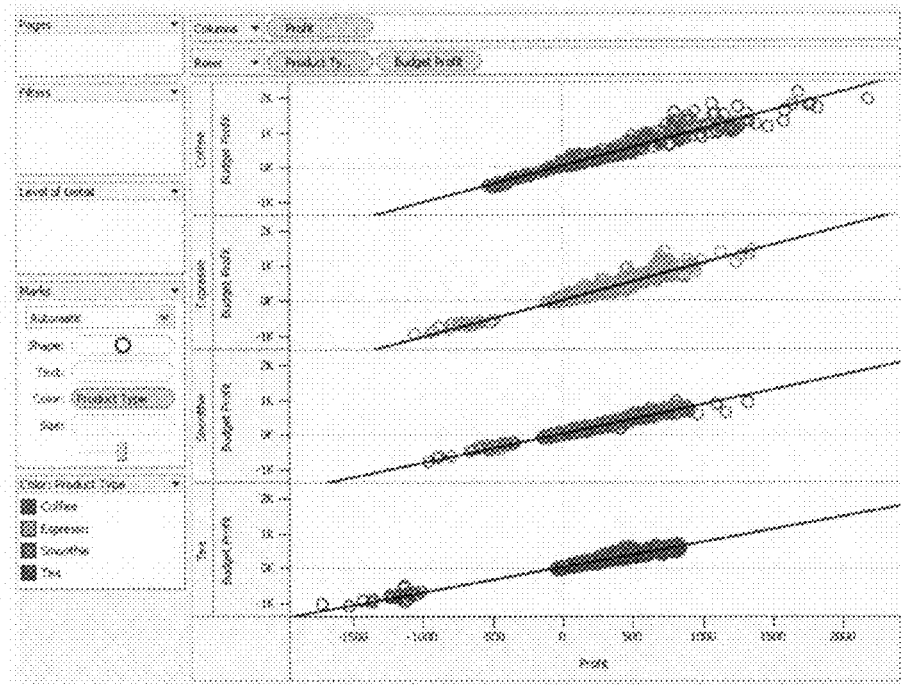
Figure 6I:
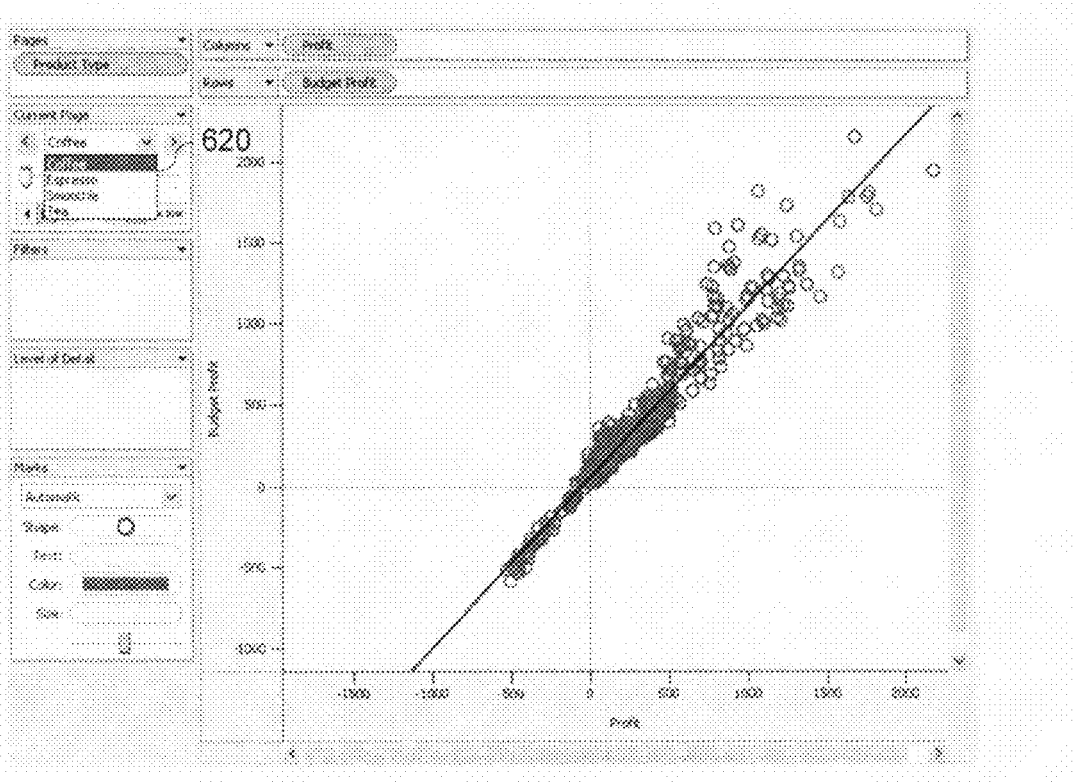
Figure 6J:
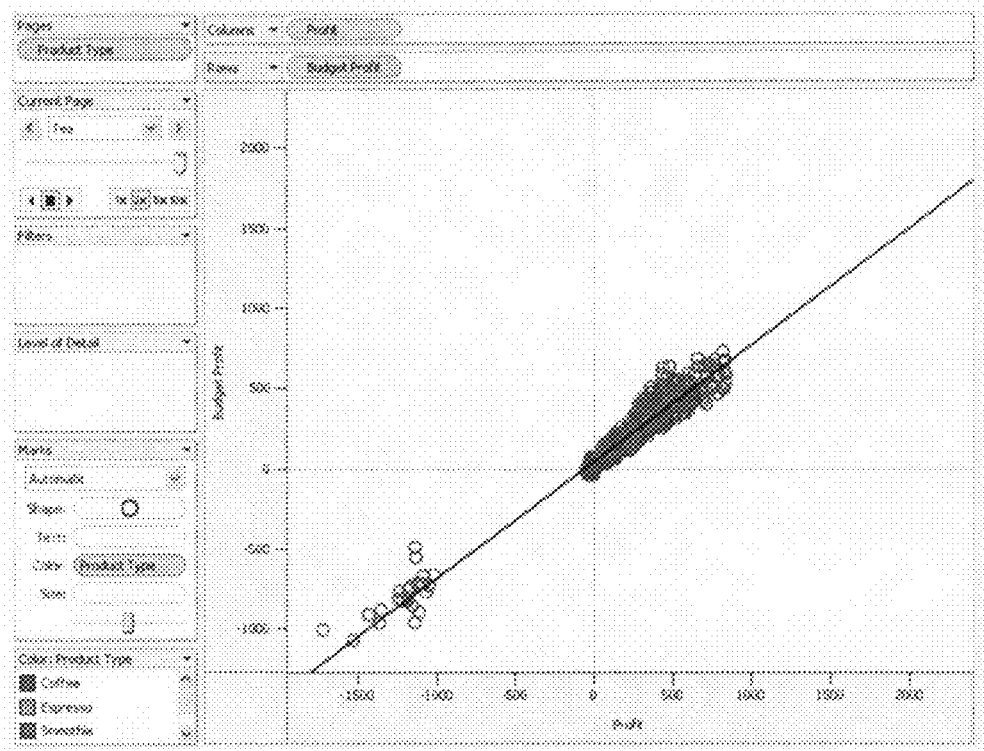
Figure 6K:
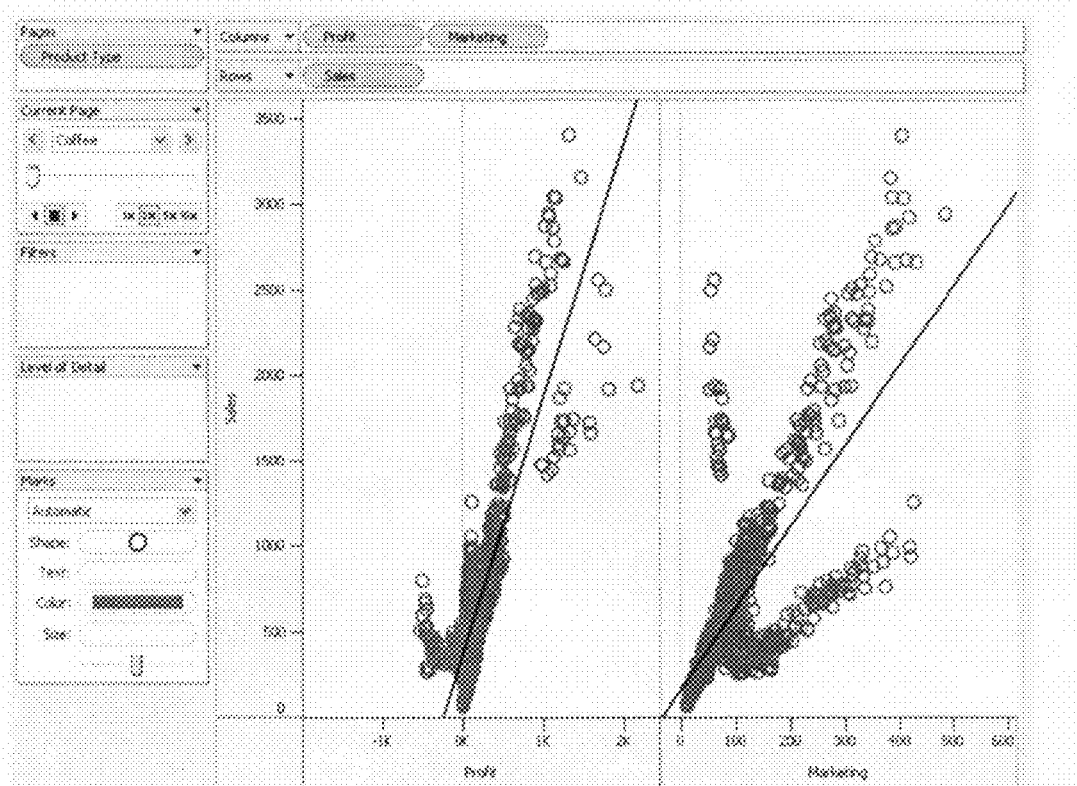
Figure 6L:
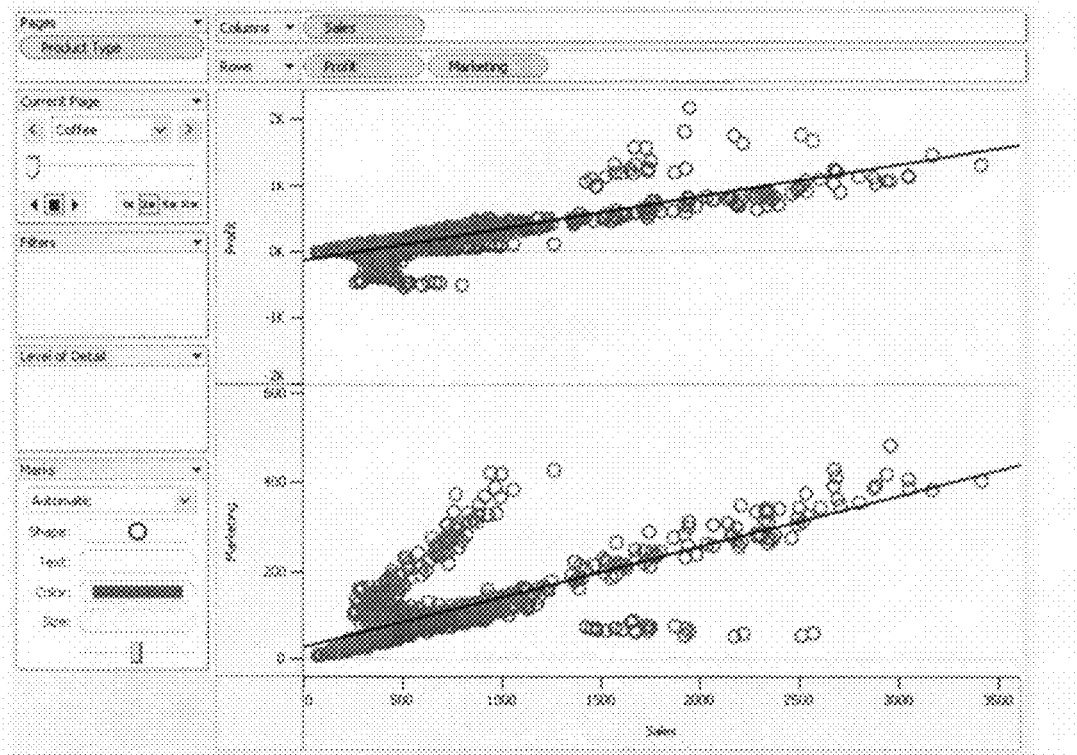
Figure 6M:
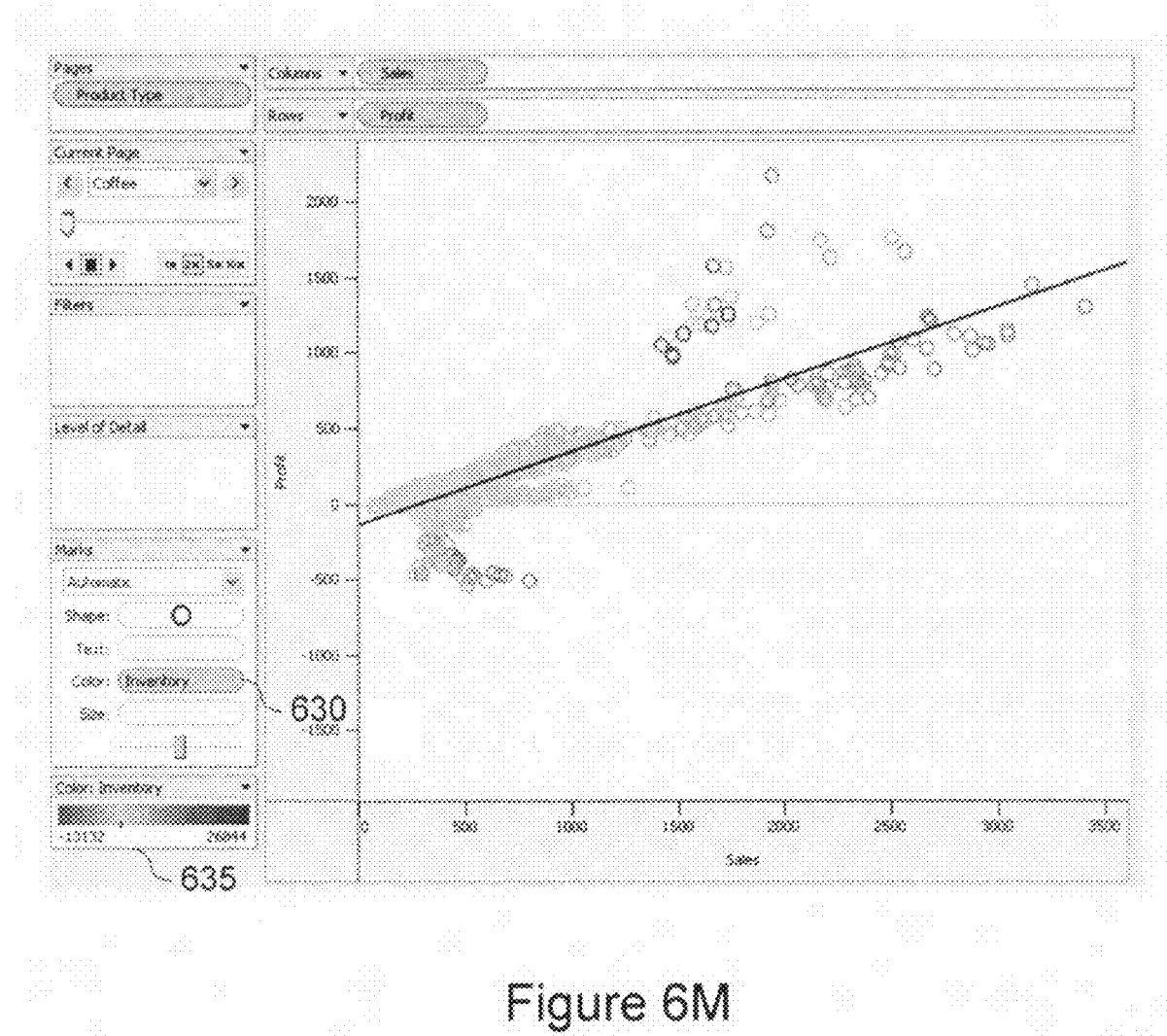
Figure 6N:
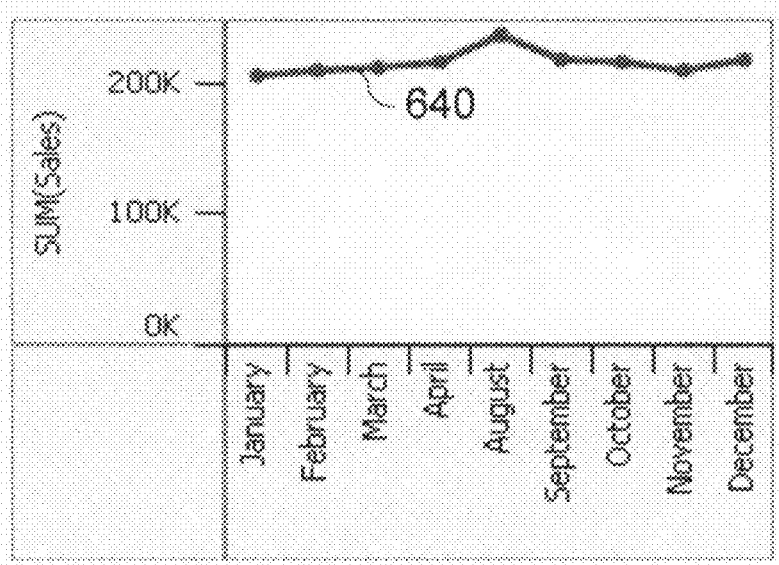
Figure 6O:
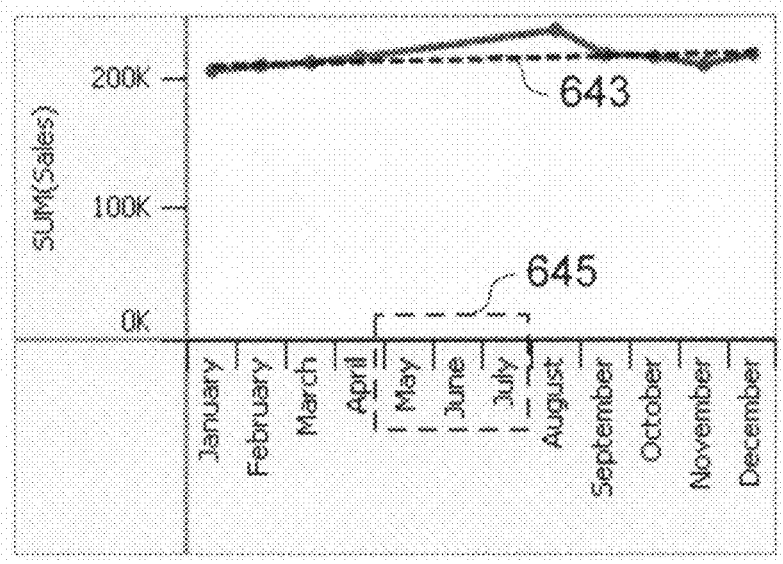
Figure 6P:
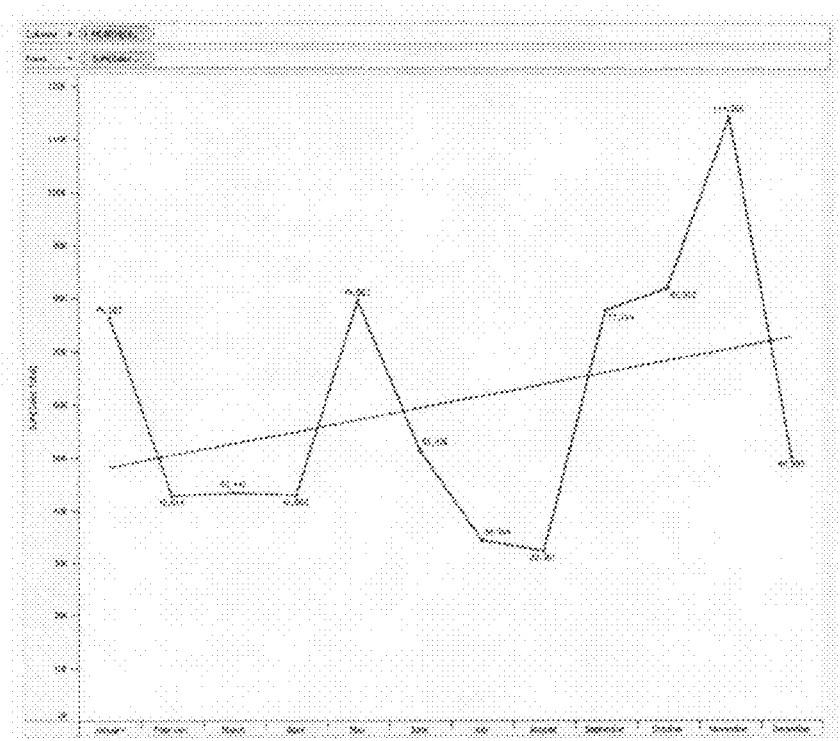
Figure 6Q:
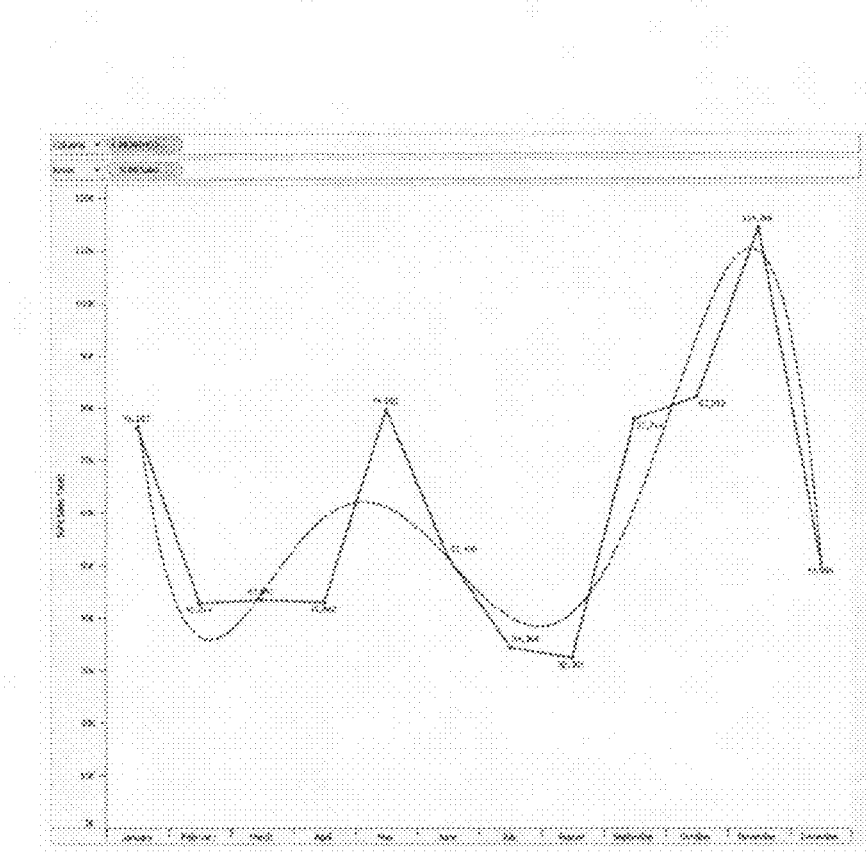

FIGS. 6A through 6Q are exemplary screenshots of different views of the dataset. The computer system generates these views and their associated model formulas, in part, by applying one or more of the aforementioned heuristics to the respective descriptions of the views.

FIG. 6A depicts a description of the dataset. The description involves three fields of the dataset. In particular, the "MONTH(Date)" field 601 is in the column field container, the "SUM(Profit)" field 603 is in the row field container and the "Product Type" field 605 is in the color field container. According to Rule Three, the "Product Type" field 605 is a categorical factor because there are more than one data points corresponding to each individual product type. Note that the "MONTH(Date)" field 601 is a categorical field, although it has a quantitative interpretation. Therefore, according to Rule One, the "SUM(Profit)" field 603 is the response variable because it is the only quantitative field in either the row or the column field container. Although the "MONTH(Date)" field 601 is a categorical field, it is the independent variable because it has a quantitative interpretation.

There is a small window 607 at the lower-left corner of FIG. 6A. The window 607 includes the color legend representing different product types with different colors. The graphical region of FIG. 6A contains four curves of different colors, curve 609 for Coffee, curve 611 for Espresso, curve 613 for Smoothie and curve 615 for Tea. Because the "MONTH(Date)" field on the horizontal axis is the independent variable and the "SUM(Profit)" field on the vertical axis in the response variable, the computer system automatically plots the curves in the left-right orientation.

Since there are independent and response variables in the description according to the heuristics, the computer system can generate a model formula in response to the user instructions. FIG. 6A depicts four dashed lines of different colors corresponding to the model formula. In particular, the dashed line 609-1 predicts the linear trend of the total profit vs. the month for Coffee. Since the "Product Type" field is a categorical factor having four members, "Coffee", "Espresso", "Smoothie", and "Tea", the computer generates a single model formula for the four product types. In some embodiments, the one model formula is replaced with four sub-model formulas, one for each product type.

FIG. 6B is a screenshot of a text-based view of the dataset corresponding to the graphical curves shown in FIG. 6A. The "MONTH(Date)" field 601 remains in the column field container. But the "Product Type" field 605 now occupies the row field container and the "SUM(Profit)" field 603 moves the text field container. The text-based table is divided into three regions 602, 604 and 606. The region 602 contains the 12 months in the "Date" field, each month occupying one column. The region 604 contains the four product types in the "Product Type" field. The region 606 contains the total profits of different product types at different months. For example, the total profits of Coffee at the 12 months are listed in the top row in the region 606. This row of data values corresponds to the curve 609 shown in FIG. 6A.

FIG. 6C depicts another description of the dataset. This description is similar to the one shown in FIG. 6A except that the "MONTH(Date)" field 601 is in the row field container and the "SUM(Profit)" field 603 is in the column field container. According to Rule Three, the "Product Type" field 605 remains to be a categorical factor. According to Rule One, the "SUM(Profit)" field 603 is the response variable because it is the only quantitative field in either the row or the column field container and the "MONTH(Date)" field 601 is the independent variable because it has a quantitative interpretation.

Because of the switch of the "MONTH(Date)" field 601 and the "SUM(Profit)" field 603, the vertical axis in FIG. 6C corresponds to the independent variable and the horizontal axis is associated with the response variable. The computer system automatically plots the four curves in a top-bottom orientation. As a result, the curves in the graphical region of FIG. 6C are rotated by 90°. Similarly, the four dashed lines of different colors corresponding to the model formula are also rotated by 90°. FIG. 6D is a screenshot of a text-based view of the dataset corresponding to the graphical curves shown in FIG. 6C. The 12 months in the region 602 are now displayed as 12 different rows. The four product types in the region 604 are now displayed as four different columns. The data in the region 606 are also rotated by 90° such that the total profits of Coffee at the 12 months are listed in the leftmost column in the region 606. This column of data values corresponds to the rightmost curve shown in FIG. 6C.

Clearly, in either example, there is no need for the user to expressly specify the two fields. Nor does the user have to instruct the computer system which fields are the respective independent and response variables. The computer system automatically figures them out by applying the relevant heuristics to the respective descriptions.

FIG. 6E depicts another description of the dataset. In this example, the "Profit" field is in the column field container, the "Budget Profit" field is in the row field container, and the "Market" field is in the color field container. According to Rule One, since both the "Profit" and "Budget Profit" fields are quantitative fields and neither is from the dimension class, the "Budget Profit" field is the response variable and the "Profit" field is the independent variable of the model formula. According to Rule Three, the "Market" field is a factor of the model formula since there are more than one data point for each market. Accordingly, the computer system generates one model formula or four sub-model formulas, one for each market. The slopes of the four colored lines indicate the accuracy of the profit predictions for the four respective geographical regions.

FIG. 6F is a screenshot of the same view after the "Profit" and "Budget Profit" fields are aggregated. Due to the summation, the computer system plots one small circle using a respective color for each geographical region. According to Rule Three, the aggregation of the "Profit" and "Budget Profit" fields renders the "Market" field no longer to be a categorical factor of the model formula because there is only one data point for each market. As a result, the computer system only generates one model formula using the remaining four data samples in the view.

FIG. 6G is a screenshot illustrating multiple views of the dataset corresponding to a single description. As shown in FIG. 6G, the column field container includes two fields, "Product Type" and "Profit", and the row field container includes one field, "Budget Profit." According to Rule Two, the "Product Type" field is a factor of the model formula because it is not the independent variable of the model formula. According to Rule One, the "Profit" field is the independent variable and the "Budget Profit" field is the response variable. The computer system generates four model formulas and displays them side by side in the alphabetical order along with their respective data views.

Similarly, the "Product Type" field is moved from the column field container to the row container in FIG. 6H. According to Rule Two, the field is still treated as a factor. The computer system generates four model formulas, one for each product type, and displays them from top to bottom in the alphabetical order along with their respective data views.

As shown in FIGS. 6I and 6J, the "Product Type" field is moved to the pages field container. According to Rule Two, this field is still treated as a factor of the model formula. The computer system, in response, generates the same four model formulas, one for each product type. The user can visualize the views of different product types separately using the drop-down menu 620. For example, the view and model formula in FIG. 6I correspond to coffee. The view and model formula in FIG. 6J correspond to tea.

FIG. 6K depicts a view of the dataset according to a description. The description includes two quantitative fields, "Profit" and "Marketing", in the column field container and one quantitative field, "Sales", in the row field container. According to Rule Four, the computer system generates two model formulas, "Sales" vs. "Profit" and "Sales" vs. "Marketing." In the description associated with FIG. 6L, the two quantitative fields, "Profit" and "Marketing", are moved to the row field container and the one quantitative field, "Sales", is move to the row field container. The computer system, accordingly, generates two model formulas, "Profit" vs. "Sales" and "Marketing" vs. "Sales." If there are M quantitative fields in the column and N quantitative fields in the row field containers, the computer system will generate M by N model formulas.

FIG. 6M is a screenshot of a view including a quantitative field, "Inventory" 630, in the color field container. According to Rule Five, a quantitative field in any encoding field container is not treated as a categorical factor. Therefore, the computer system generates a single model formula for the view of the dataset. A small window 635 in the screenshot includes a color spectrum, different color values in the spectrum corresponding to different inventory values. The computer system plots different circles using different color values based upon the inventory values associated with the circles.

Statistical modeling can not only predict the trend of two correlating fields but also provide values missing from a dataset. FIG. 6N depicts a curve 640 illustrating the total sales revenue as a function of the month. However, a close look at the horizontal axis reveals that the total sales revenues associated with May, June and July are missing from the curve 640. According to Rule Six, the computer system generates a model formula using the remaining data shown in the figure. FIG. 6O depicts a diagram including a line 643 representing the model formula. The diagram includes not only the existing data shown in FIG. 6N but also the three months 645 that are missing in FIG. 6N.

Given a dataset and a user-provided description of a view of the dataset, the computer system can generate different types of model formulas including linear, polynomial, exponential, logarithmic, transcendental and other mathematical functions. In most occasions, a model formula based on the linear regression gives the user a reasonable insight into the dataset. But in some cases, the user may be interested in simulating the data using a more complex model.

FIGS. 6P and 6Q depict two types of model formulas, respectively. The linear relationship shown in FIG. 6P indicates that there is a growing trend for the total sales revenue throughout the whole year. But the 5-degree polynomial in FIG. 6Q captures the up and down of the total sales revenue within the year. On the face, the polynomial seems to a closer fit of the actual data than the linear trend. However, this does not guarantee that the polynomial can provide the user with more insight into the dataset.

In some embodiments, the computer system automatically generates multiple model formulas for the same dataset. The multiple model formulas may correspond to different model types and/or have different degrees of freedom or different numbers of parameters for the same model type. Next, the computer system automatically selects one or several of the multiple model formulas that have fewer parameters, but still provide a good fit of the dataset according to one or more predefined criteria (e.g., in a visualization sense). Sometimes, this selection process may need some level of user guidance. In this case, the computer system provides an interface for a user to offer input, e.g., by excluding some model types from the selection process. As a result, model formulas that uses simpler models, but fit nearly as well as more complicated models, are chosen to represent the dataset. A simpler model formula makes it easier for the user to make informed predictions from the available data.

In some other embodiments, a user does not need to expressly provide a description of a view of the dataset. Rather, the user just selects a set of fields that the user is interested in. Based on the user-selected fields of interest, the computer system automatically creates one or more descriptions, each description including a subset of the selected fields of interest. As noted above, each field of a description should be associated with one of the multiple field containers. In order to find the most appropriate field containers for each field of interest, the computer system determines the properties of the fields of interest and calculates the dependencies between different fields based on their respective properties. After taking into account of various information items including the properties, the dependencies between fields, the field types and classes and the categorical field cardinalities, the computer system selects one or more descriptions that provide best views of the dataset. In some embodiments, the computer system also generates the model formulas associated with the descriptions and analyzes these model formulas to select the view(s) in which the model formulas fit the dataset or a subset of the dataset particularly well.

As noted above, the generation of model formulas is essentially statistical modeling. Therefore, in some embodiments, the computer system not only generates and displays the model formulas but also provide a set of statistical measures associated with the model formulas and the dataset. For example, one statistical measure is the residual between a model formula and the source data used for estimating the model formula. When a user drops this statistical measure into the color field container, the computer system can color the source data according to their respective residual values, i.e., the distance between the source data and the model formulas. One skilled in the art will understand that there are many possible statistical measures include residual, residual squared, P-value, slope (only available for linear fitting), and model formula predicted values, etc.

The present invention not only accepts datasets and databases as inputs, it also accepts views as inputs. A view can be used to represent a set of fields. For example, rules or operators can take into account the current view to generate a new view that is related to the current view. Also, as one skilled in the art will realize, many other rules are possible, including ones for generating multi-dimensional model formulas like $y=f(x_1, x_2, \ldots, x_N)$.

The present invention can be implemented as a computer program product that comprises a computer program mechanism embedded in a computer readable storage medium. For instance, the computer program product could contain the program modules shown in FIG. 2. These program modules may be stored on a CD-ROM, magnetic disk storage product, or any other computer readable data or program storage product. The software modules in the computer program product can also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of automatically generating statistical models for a dataset, comprising:
    at a computer system having one or more processors and memory storing programs executed by the one or more processors:
    receiving a user description of a graphical view of a dataset, wherein the user description specifies a graphical relationship between a first field and a second field of the dataset in the graphical view;
    determining a set of data properties for each of the first and second fields;
    with no further user input, generating one or more statistical models of the dataset in accordance with the data properties of the first and second fields and data values associated with the first and second fields in the dataset, wherein the one or more statistical models are derived from the data values and are expressed in one or more mathematical equations for describing and predicting a respective trend of one of the first and second fields that varies as a function of the other of the first and second fields; and
    displaying at least one graphical representation of the one or more statistical models in the graphical view of the dataset.

2. The method of claim 1, wherein the first and second fields are partitioned into a plurality of sets, each set associated with a respective region of the view including row, column, page, and an encoding area.

3. The method of claim 2, wherein the data properties of each field include a field type selected from the group consisting of categorical and quantitative and a data type selected from the group consisting of integer, real, Boolean, and time.

4. The method of claim 3, further comprising generating the one or more statistical models in accordance with predefined heuristics for modeling a relationship between the first field and the second field wherein the predefined heuristics include: selecting one of the two fields from the user description as an independent variable and the other of the two fields as a response variable of the one or more statistical models, and converting categorical fields in the user description into factors of the one or more statistical models.

5. The method of claim 4, wherein the predefined heuristics further comprise:
    defining a first quantitative field on the row (or the column) as a response variable and a second field on the column (or the row) as an independent variable if the first quantitative field is the only quantitative field on the row or the column of the view and the second field is either a quantitative field or a categorical field having a quantitative interpretation; and
    generating the one or more statistical models using data in the dataset associated with the response variable and the independent variable.

6. The method of claim 4, wherein the predefined heuristics further comprise:
    defining a first quantitative field on the row (or the column) as a response variable and a second quantitative field on the column (or the row) as an independent variable if the second quantitative field is a quantitative field from a dimension class; and
    generating the one or more statistical models using data in the dataset associated with the response variable and the independent variable.

7. The method of claim 4, wherein the predefined heuristics further comprise:
    defining a first quantitative field on the row as a response variable and a second quantitative field on the column as an independent variable; and
    generating the one or more statistical models using data in the dataset associated with the response variable and the independent variable.

8. The method of claim 7, wherein the predefined heuristics further comprise:
    repeating said defining and generating steps for each unique pair of first and second quantitative fields on the column and row.

9. The method of claim 4, wherein the predefined heuristics further comprise:
    defining each categorical field on the row, the column and the page of the view as a categorical factor of the one or more statistical models.

10. The method of claim 4, wherein the predefined heuristics further comprise:
defining each categorical field in the encoding area as a categorical factor of the one or more statistical models if there are more than one data points corresponding to each value in the categorical field.

11. The method of claim 4, wherein the predefined heuristics further comprise:
disregarding each quantitative field in the encoding area of the view from the factors of the one or more statistical models.

12. The method of claim 1, wherein each of the one or more statistical models has a model type including linear, polynomial, exponential, logarithmic, and transcendental.

13. The method of claim 1, wherein the user description is generated by a user dragging and dropping the first and second fields into respective field containers of a graphical user interface.

14. The method of claim 1, wherein the user description is generated by a user selecting the first and second fields as fields of interest through a graphical user interface.

15. The method of claim 1, wherein the user description is generated by a user entering a text string including the first and second fields as fields of interest through a user interface.

16. The method of claim 1, wherein the one or more statistical models are derived in accordance with one or more mathematical theories selected from the group consisting of regression, clustering, summarization, dependency modeling, and classification.

17. A method of automatically generating models for a dataset, comprising:
at a computer system having one or more processors and memory storing programs executed by the one or more processors:
allowing a user to provide a user description by dragging and dropping fields into field containers of a graphical user interface to generate a graphical view of the dataset, the user description including at least two sets of fields associated with the graphical view of the dataset;
determining a set of data properties for each of the two sets of fields;
with no further user input, generating one or more statistical models based on the properties of the two sets of fields, data values associated with the two sets of fields, and a set of predefined heuristics for defining a relationship between a first field from one of the two sets of fields and a second field from the other of the two sets of fields, wherein the one or more statistical models are derived from the data values and are expressed in one or more mathematical equations for describing and predicting a respective trend of one of the first and second fields that varies as a function of the other of the first and second fields; and
displaying at least one graphical representation of the one or more statistical models in a specific region of the graphical user interface.

18. The method of claim 17, wherein each set of fields is associated with a respective region of the view including row, column, page, and an encoding area.

19. The method of claim 18, wherein each field includes a field type selected from the group consisting of categorical and quantitative and a data type selected from the group consisting of integer, real, Boolean, and time.

20. The method of claim 19, wherein the set of predefined heuristics includes selecting one of the two fields from the user description as an independent variable and the other of the two fields as a response variable of the one or more statistical models, and converting categorical fields in the user description into factors of the one or more statistical models.

21. The method of claim 20, wherein the set of predefined heuristics further comprises:
defining a first quantitative field on the row (or the column) as a response variable and a second field on the column (or the row) as an independent variable if the first quantitative field is the only quantitative field on the row or the column of the view and the second field is either a quantitative field or a categorical field having a quantitative interpretation; and
generating the one or more statistical models using data in the dataset associated with the response variable and the independent variable.

22. The method of claim 20, wherein the set of predefined heuristics further comprises:
defining a first quantitative field on the row (or the column) as a response variable and a second quantitative field on the column (or the row) as an independent variable if the second quantitative field is a quantitative field from a dimension class; and
generating the one or more statistical models using data in the dataset associated with the response variable and the independent variable.

23. The method of claim 20, wherein the set of predefined heuristics further comprises:
defining a first quantitative field on the row as a response variable and a second quantitative field on the column as an independent variable; and
generating the one or more statistical models using data in the dataset associated with the response variable and the independent variable.

24. The method of claim 23, wherein the set of predefined heuristics further comprises:
repeating said defining and generating steps for each unique pair of first and second quantitative fields on the column and row.

25. The method of claim 20, wherein the set of predefined heuristics further comprises:
defining each categorical field on the row, the column and the page of the view as a categorical factor of the one or more statistical models.

26. The method of claim 20, wherein the set of predefined heuristics further comprises:
defining each categorical field in the encoding area as a categorical factor of the one or more statistical models if there are more than one data points corresponding to each value in the categorical field.

27. The method of claim 20, wherein the set of predefined heuristics further comprises:
disregarding each quantitative field in the encoding area of the view from the factors of the one or more statistical models.

28. The method of claim 17, wherein each of the one or more statistical models has a model type including linear, polynomial, exponential, logarithmic, and transcendental.

29. The method of claim 17, wherein the user description is generated by a user dragging and dropping a subset of the two sets of fields into respective field containers of a graphical user interface.

30. The method of claim 17, wherein the user description is generated by a user selecting a subset of the two sets of fields as fields of interest through a graphical user interface.

31. The method of claim 17, wherein the user description is generated by a user entering a text string including a subset of the two sets of fields as fields of interest through a user interface.

32. The method of claim 17, wherein the one or more statistical models are derived in accordance with one or more mathematical theories selected from the group consisting of regression, clustering, summarization, dependency modeling, and classification.

33. A computer system, comprising:
a main memory;
a processor; and
at least one program, stored in the main memory and executed by the processor, the at least one program further including:
instructions for receiving a user description to generate a graphical view of a dataset, wherein the user description specifies a graphical relationship between a first field and a second field of the dataset in the graphical view;
instructions for determining a set of data properties for each of the first and second fields;
instructions for generating one or more statistical models in accordance with the respective data properties of the first and second fields and data values that are associated with the first and second fields in the dataset with no further user input, wherein the one or more statistical models are derived from the data values and are expressed in one or more mathematical equations for describing and predicting a respective trend of one of the first and second fields that varies as a function of the other of the first and second fields; and
instructions for displaying at least one graphical representation of the one or more statistical models in the graphical view of the dataset.

34. The computer system of claim 33, wherein the first and second fields are partitioned into a plurality of sets, each set associated with a respective region of the view including row, column, page, and an encoding area.

35. The computer system of claim 34, wherein the data properties of each field include a field type selected from the group consisting of categorical and quantitative and a data type selected from the group consisting of integer, real, Boolean, and time.

36. The computer system of claim 35, further comprising instructions for generating the one or more statistical models in accordance with predefined heuristics for modeling a relationship between the first field and the second field wherein the predefined heuristics include instructions for selecting one of the two fields from the user description as an independent variable and the other of the two fields as a response variable of the one or more statistical models, and instructions for converting categorical fields in the user description into factors of the one or more statistical models.

37. The computer system of claim 36, wherein the predefined heuristics further comprise:
instructions for defining a first quantitative field on the row (or the column) as a response variable and a second field on the column (or the row) as an independent variable if the first quantitative field is the only quantitative field on the row or the column of the view and the second field is either a quantitative field or a categorical field having a quantitative interpretation; and
instructions for generating the one or more statistical models using data in the dataset associated with the response variable and the independent variable.

38. The computer system of claim 36, wherein the predefined heuristics further comprise:
instructions for defining a first quantitative field on the row (or the column) as a response variable and a second quantitative field on the column (or the row) as an independent variable if the second quantitative field is a quantitative field from a dimension class; and
instructions for generating the one or more statistical models using data in the dataset associated with the response variable and the independent variable.

39. The computer system of claim 36, wherein the predefined heuristics further comprise:
instructions for defining a first quantitative field on the row as a response variable and a second quantitative field on the column as an independent variable; and
instructions for generating the one or more statistical models using data in the dataset associated with the response variable and the independent variable.

40. The computer system of claim 39, wherein the predefined heuristics further comprise:
instructions for repeating said defining and generating instructions for each unique pair of first and second quantitative fields on the column and row.

41. The computer system of claim 36, wherein the predefined heuristics further comprise:
instructions for defining each categorical field on the row, the column and the page of the view as a categorical factor of the one or more statistical models.

42. The computer system of claim 36, wherein the predefined heuristics further comprise:
instructions for defining each categorical field in the encoding area as a categorical factor of the one or more statistical models if there are more than one data points corresponding to each value in the categorical field.

43. The computer system of claim 36, further comprising:
instructions for disregarding each quantitative field in the encoding area of the view from the factors of the one or more statistical models.

44. The computer system of claim 33, wherein each of the one or more statistical models has a model type including linear, polynomial, exponential, logarithmic, and transcendental.

45. The computer system of claim 33, wherein the user description is generated by a user dragging and dropping the first and second fields into respective field containers of a graphical user interface.

46. The computer system of claim 33, wherein the user description is generated by a user selecting the first and second fields as fields of interest through a graphical user interface.

47. The computer system of claim 33, wherein the user description is generated by a user entering a text string including the first and second fields as fields of interest through a user interface.

48. The computer system of claim 33, wherein the one or more statistical models are derived in accordance with one or more mathematical theories selected from the group consisting of regression, clustering, summarization, dependency modeling, and classification.

49. A computer program product for use in conjunction with a computer system that includes one or more processors and memory, the computer program product comprising a computer readable storage medium and a computer program mechanism embedded therein, the computer program mechanism comprising instructions that, if executed by the computer system, cause the computer system to:
receive a user description of a graphical view of a dataset, wherein the user description specifies a graphical relationship between a first field and a second field of the dataset in the graphical view;

determine a set of data properties for each of the first and second fields;

generate one or more statistical models of the dataset in accordance with the data properties of the first and second fields and data values associated with the first and second fields in the dataset with no further user input, wherein the one or more statistical models are derived from the data values and are expressed in one or more mathematical equations for describing and predicting a respective trend of one of the first and second fields that varies as a function of the other of the first and second fields; and display at least one graphical representation of the one or more statistical models in the graphical view of the dataset.

50. The computer program product of claim 49, wherein the first and second fields are partitioned into a plurality of sets, each set associated with a respective region of the view including row, column, page, and an encoding area.

51. The computer program product of claim 50, wherein the data properties of each field include a field type selected from the group consisting of categorical and quantitative and a data type selected from the group consisting of integer, real, Boolean, and time.

52. The computer program product of claim 51, further comprising instructions for generating the one or more statistical models in accordance with predefined heuristics for modeling a relationship between the first field and the second field wherein the predefined heuristics include instructions for selecting one of the two fields from the user description as an independent variable and the other of the two fields as a response variable of the one or more statistical models, and instructions for converting categorical fields in the user description into factors of the one or more statistical models.

53. The computer program product of claim 52, wherein the predefined heuristics further comprise:

instructions for defining a first quantitative field on the row (or the column) as a response variable and a second field on the column (or the row) as an independent variable if the first quantitative field is the only quantitative field on the row or the column of the view and the second field is either a quantitative field or a categorical field having a quantitative interpretation; and instructions for generating the one or more statistical models using data in the dataset associated with the response variable and the independent variable.

54. The computer program product of claim 52, wherein the predefined heuristics further comprise:

instructions for defining a first quantitative field on the row (or the column) as a response variable and a second quantitative field on the column (or the row) as an independent variable if the second quantitative field is a quantitative field from a dimension class; and instructions for generating the one or more statistical models using data in the dataset associated with the response variable and the independent variable.

55. The computer program product of claim 52, wherein the predefined heuristics further comprise:

instructions for defining a first quantitative field on the row as a response variable and a second quantitative field on the column as an independent variable; and instructions for generating the one or more statistical models using data in the dataset associated with the response variable and the independent variable.

56. The computer program product of claim 55, wherein the predefined heuristics further comprise:

instructions for repeating said defining and generating instructions for each unique pair of first and second quantitative fields on the column and row.

57. The computer program product of claim 52, wherein the predefined heuristics further comprise:

instructions for defining each categorical field on the row, the column and the page of the view as a categorical factor of the one or more statistical models.

58. The computer program product of claim 52, wherein the predefined heuristics further comprise:

instructions for defining each categorical field in the encoding area as a categorical factor of the one or more statistical models if there are more than one data points corresponding to each value in the categorical field.

59. The computer program product of claim 52, wherein the predefined heuristics further comprise:

instructions for disregarding each quantitative field in the encoding area of the view from the factors of the one or more statistical models.

60. The computer program product of claim 49, wherein each of the one or more statistical models has a model type including linear, polynomial, exponential, logarithmic, and transcendental.

61. The computer program product of claim 49, wherein the user description is generated by a user dragging and dropping the first and second fields into respective field containers of a graphical user interface.

62. The computer program product of claim 49, wherein the user description is generated by a user selecting the first and second fields as fields of interest through a graphical user interface.

63. The computer program product of claim 49, wherein the user description is generated by a user entering a text string including the first and second fields as fields of interest through a user interface.

64. The computer program product of claim 49, wherein the one or more statistical models are derived in accordance with one or more mathematical theories selected from the group consisting of regression, clustering, summarization, dependency modeling, and classification.

65. A computer system comprising:
a main memory;
a processor; and
at least one program, stored in the main memory and executed by the processor, the at least one program further including:
means for receiving a user description to generate a graphical view of a dataset, wherein the user description specifies a graphical relationship between a first field and a second field of the dataset in the graphical view
means for determining a set of data properties for each of the first and second fields; and
means for generating one or more statistical models in accordance with the respective data properties of the first and second fields and data values that are associated with the first and second fields in the dataset with no further user input, wherein the one or more statistical models are derived from the data values and are expressed in one or more mathematical equations for describing and predicting a respective trend of one of the first and second fields that varies as a function of the other of the first and second fields; and
means for displaying at least one graphical representation of the one or more statistical models in the graphical view of the dataset.

66. The computer system of claim 65, wherein the one or more statistical models are derived in accordance with one or more mathematical theories selected from the group consisting of regression, clustering, summarization, dependency modeling, and classification.

* * * * *